(12) United States Patent
Mintzer et al.

(10) Patent No.: US 11,828,891 B2
(45) Date of Patent: Nov. 28, 2023

(54) SILICON PHOTOMULTIPLIER BASED TOF-PET DETECTOR

(71) Applicant: Siemens Medical Solutions USA, Inc., Malvern, PA (US)

(72) Inventors: Robert A. Mintzer, Knoxville, TN (US); James Christopher Arnott, Knoxville, TN (US); Mehmet Aykac, Knoxville, TN (US); Johannes Breuer, Forchheim (DE); Sanghee Cho, Knoxville, TN (US); Peter Hansen, Knoxville, TN (US); Maciej P. Kapusta, Knoxville, TN (US); James L. Corbeil, Knoxville, TN (US); Nan Zhang, Knoxville, TN (US)

(73) Assignee: Siemens Medical Solutions USA, Inc., Malvern, PA (US)

( * ) Notice: Subject to any disclaimer, the term of this patent is extended or adjusted under 35 U.S.C. 154(b) by 472 days.

(21) Appl. No.: 16/596,901

(22) Filed: Oct. 9, 2019

(65) Prior Publication Data
US 2020/0041665 A1     Feb. 6, 2020

Related U.S. Application Data

(63) Continuation of application No. 14/244,312, filed on Apr. 3, 2014, now Pat. No. 10,527,740.

(51) Int. Cl.
*G01T 1/20*     (2006.01)
*G01T 1/208*     (2006.01)
(Continued)

(52) U.S. Cl.
CPC .............. *G01T 1/208* (2013.01); *A61B 6/037* (2013.01); *A61B 6/4233* (2013.01);
(Continued)

(58) Field of Classification Search
None
See application file for complete search history.

(56) References Cited

U.S. PATENT DOCUMENTS

| 7,019,297 | B2 | 3/2006 | Aykac et al. |
| 7,408,164 | B2 | 8/2008 | Schmand et al. |

(Continued)

OTHER PUBLICATIONS

M. Conti et al., "Estimating image quality for future generations of TOF PET scanners," 2011 IEEE Nuclear Science Symposium Conference Record MIC9.S-25, pp. 2407-2414.

(Continued)

*Primary Examiner* — Patricia J Park

(57) ABSTRACT

A scintillation block detector employs an array of optically air coupled scintillation pixels, the array being wrapped in reflector material and optically coupled to an array of silicon photomultiplier light sensors with common-cathode signal timing pickoff and individual anode signal position and energy determination. The design features afford an optimized combination of photopeak energy event sensitivity and timing, while reducing electronic circuit complexity and power requirements, and easing necessary fabrication methods. Four of these small blocks, or "miniblocks," can be combined as optically and electrically separated quadrants of a larger single detector in order to recover detection efficiency that would otherwise be lost due to scattering between them. Events are validated for total energy by summing the contributions from the four quadrants, while the trigger is generated from either the timing signal of the quadrant with the highest energy deposition, the first timing signal derived from the four quadrant time-pickoff signals, or a statistically optimum combination of the individual quadrant event times, so as to maintain good timing for scatter events. This further reduces the number of electronic channels required per unit detector area while avoiding the (Continued)

timing degradation characteristic of excessively large SiPM arrays.

19 Claims, 28 Drawing Sheets

(51) Int. Cl.
| | |
|---|---|
| *G01T 1/29* | (2006.01) |
| *A61B 6/03* | (2006.01) |
| *G01T 1/164* | (2006.01) |
| *A61B 6/00* | (2006.01) |
| *G01T 1/16* | (2006.01) |
| *G01R 33/48* | (2006.01) |

(52) U.S. Cl.
CPC .......... *A61B 6/4241* (2013.01); *A61B 6/4258* (2013.01); *G01T 1/1606* (2013.01); *G01T 1/1647* (2013.01); *G01T 1/20183* (2020.05); *G01T 1/20184* (2020.05); *G01T 1/20185* (2020.05); *G01T 1/2985* (2013.01); *A61B 6/032* (2013.01); *A61B 6/4417* (2013.01); *G01R 33/481* (2013.01)

(56) References Cited

U.S. PATENT DOCUMENTS

| | | | |
|---|---|---|---|
| 2008/0042070 A1* | 2/2008 | Levin | H04N 5/32 250/370.1 |
| 2009/0134334 A1* | 5/2009 | Nelson | G01T 1/2002 250/361 R |
| 2010/0270462 A1 | 10/2010 | Nelson et al. | |
| 2011/0017916 A1 | 1/2011 | Schulz et al. | |
| 2011/0210255 A1 | 9/2011 | Kim et al. | |
| 2012/0025074 A1* | 2/2012 | Barbi | G01N 23/2257 250/307 |
| 2012/0061576 A1 | 3/2012 | Degenhardt et al. | |
| 2012/0199748 A1 | 8/2012 | Cooke et al. | |
| 2013/0009066 A1* | 1/2013 | Grazioso | G01T 1/1642 250/363.03 |
| 2013/0168566 A1* | 7/2013 | Blackburn | G01T 1/22 250/391 |
| 2013/0327932 A1 | 12/2013 | Kim et al. | |
| 2014/0231655 A1* | 8/2014 | Dueppenbecker | G01T 1/2985 250/366 |
| 2015/0168567 A1* | 6/2015 | Kim | G01T 1/248 250/370.11 |
| 2016/0084703 A1* | 3/2016 | Shaber | G01T 1/248 250/336.1 |
| 2016/0097866 A1* | 4/2016 | Williams | G01T 1/249 250/362 |

OTHER PUBLICATIONS

C. Piemonte et al., "Timing performance of large area SiPMs coupled to LYSO using dark noise compensation methods," NSS/MIC IEEE 2011, pp. 59-63.

A. Gola et al., "Analog circuit for timing measurements with large area SiPMs coupled to LYSO crystals," NSS/MIC IEEE 2011, pp. 725-731.

Knoll, G. F.: Radiation Detection and Measurement. 4th ed. Hoboken : John Wiley & Sons, Inc., 2010 , ISBN 978-0-470-13148-0 (entire book) (description enclosed).

Szczesniak, T., et al., "MPPC arrays in PET detectors with LSO and BGO scintillators," Nuclear Science Symposium and Medical Imaging Conference (NSS/MIC), 2011 IEEE , pp. 3272-3278, Oct. 23-29, 2011.

* cited by examiner

SILICON PHOTOMULTIPLIER BASED TOF-PET DETECTOR

CROSS REFERENCE TO RELATED APPLICATIONS

This application is a continuation of U.S. patent application Ser. No. 14/244,312 filed on Apr. 3, 2014 the contents are which are hereby incorporated by reference.

BACKGROUND OF THE INVENTION

1. Field of the Invention

The present invention relates generally to nuclear medical imaging, and in particular relates to scintillation detectors used in Positron Emission Tomography (PET).

2. Description of the Related Art

Silicon photomultipliers (SiPMs) can be used to improve the timing performance of positron emission tomography (PET) detectors over that achievable with conventional vacuum tube photomultipliers (PMTs). Some of the properties of these devices contributing to this are the high photon detection efficiency (PDE), a combination of high microcell fill factor and very high quantum efficiency (QE), high uniformity of microcell gain and good single photon time response. The small size of SiPMs allows finer sampling of pixelated or monolithic scintillator blocks, even down to one-to-one coupling of light sensor and scintillator pixel. This can reduce the light spread to the sensors required for event positioning which can result in significantly lower light path length and path length variance, and thus reduce timing jitter for low level leading edge discriminator timing methods. In addition, the SiPM shape (typically square or rectangular) and high active area percentage results in much higher geometric fill factor on a scintillator block than can be achieved with PMTs. The resulting increase in light collection efficiency improves initial photon collection and thus timing performance.

One possible method of exploiting these facts is to optically couple each scintillator pixel in a detector block to one SiPM. However, a number of practical and technical issues make this both difficult and sub-optimal for total PET system performance. A PET system using such 1:1 coupling would have to have tens of thousands of high timing performance, high power electronics channels. Scatter of 511 keV gammas between scintillator pixels is frequent, and although a system design might recover adjacent coincident events adding to the total energy, this would add to complexity and high electronic density and power, and some timing resolution loss for these events is inevitable. Cost effective and reliable monolithic arrays of SiPMs and arrays of discrete SiPMs in multi-device packaging have optical coupling between devices in the packaging optical window, which can degrade timing performance seen in one device/pixel channel. Optical reflector materials between every pixel result in light losses from the high aspect ratio of the pixel (due to the many reflections) which can lead to timing degradation, and lower packing fraction of scintillator, causing a loss of detective solid angle and thus system sensitivity reduction. These problems are not admitted to have been known in the prior art by inclusion in this section.

Information relevant to attempts to address these problems can be found in the following references, which are not admitted to be prior art with respect to the present invention by inclusion in this section:

(1) M. Conti et. al., "Estimating image quality for future generations of TOF PET scanners," 2011 IEEE Nuclear Science Symposium Conference Record MIC9.S-25;
(2) C. Piemonte et. al, "Timing performance of large area SiPMs coupled to LYSO using dark noise compensation methods," NSS/MIC IEEE 2011;
(3) A. Cola et. al, "Analog circuit for timing measurements with large area SiPMs coupled to LYSO crystals," NSS/MIC IEEE 2011;
(4) G. F. Knoll, Radiation Detection and Measurement, 2nd Edition, John Wiley & Sons, Inc., 2010, pages 65-104;
(5) U.S. Pat. No. 7,019,297 B2 "Detector Array Using Internalized Light Sharing and Air Coupling";
(6) U.S. Pat. No. 7,408,164 B2 "Detector Array Utilizing Air Gaps as a Reflector Between Array Elements";
(7) US 2011/0210255 A1 "Multiplexing Readout Scheme for a Gamma Ray Detector";
(8) US 2011/0017916 A1 "Reflector and Light Collimator Arrangement for Improved Light Collection in Scintillation Detectors";
(9) US 2012/0061576 A1 "PET Detector System with Improved Capabilities for Quantification"; and
(10) US 2012/0199748 A1 "Radiation Conversion Elements with Reflectors for Radiological Imaging Apparatus."

A need exists to construct optically coupled arrays of scintillators on SiPM arrays such that the coincidence resolving time and total energy event capture sensitivity are optimized together—that is, to design small detector blocks or "miniblocks," that are large enough to capture a high fraction of events without scatter losses outside them, while maintaining the best timing performance possible. The remaining smaller fraction of 511 keV events that still scatter between these miniblocks would then need to be recovered by a practical method of detecting full photopeak energy events while generating the best timing available from the individual miniblock signals.

BRIEF SUMMARY OF THE INVENTION

Various embodiments relate to a scintillation block detector that employs an array of optically air-coupled scintillation pixels, the array being wrapped in reflector material and optically coupled to an array of silicon photomultiplier (SiPM) light sensors with common-cathode signal timing pickoff and individual anode signal position and energy determination. The design features afford an optimized combination of photopeak energy event sensitivity and timing, while reducing electronic circuit complexity and power requirements, and easing necessary fabrication methods. Four of these small blocks, or "miniblocks," can be combined as optically and electrically separated quadrants of a larger single detector in order to recover detection efficiency that would otherwise be lost due to scattering between them. Events are validated for total energy by summing the contributions from the four quadrants, while the trigger is generated from either the timing signal of the quadrant with the highest energy deposition, the first timing signal derived from the four quadrant time-pickoff signals, or a statistically optimum combination of the individual quadrant event times, so as to maintain good timing for scatter events. This further reduces the number of electronic channels required per unit detector area while avoiding the timing degradation characteristic of excessively large SiPM arrays.

BRIEF DESCRIPTION OF THE DRAWINGS

These and other features, aspects, and advantages of the present invention will become better understood with reference to the following description and appended claims, and accompanying drawings where:

FIG. 6B shows a much smaller difference in trigger time when using energy normalization techniques;

Figure 1:
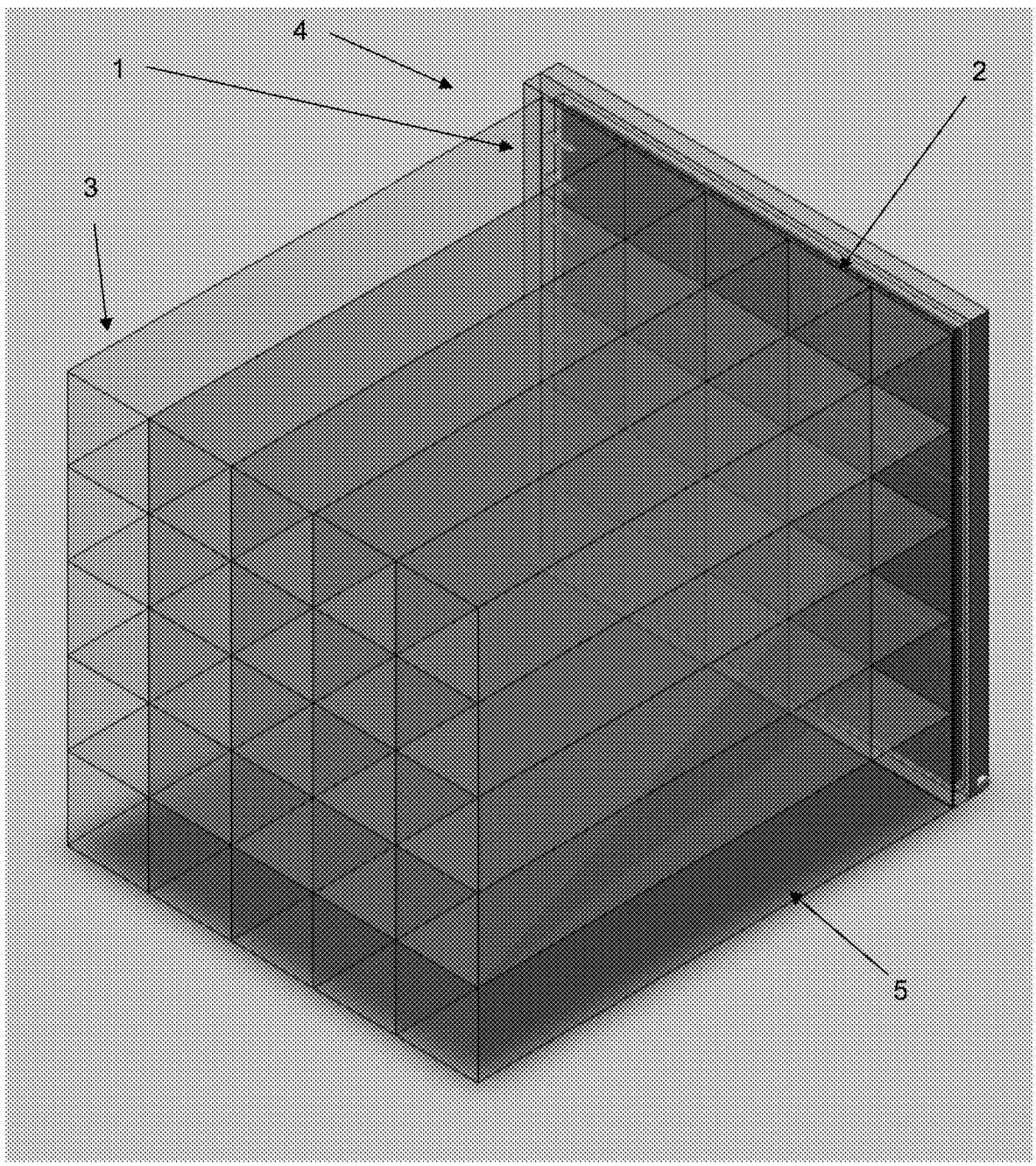
FIG. 1: is a schematic diagram of a block of air-coupled pixels on a common-cathode SiPM light sensor array.

It should be understood that the various embodiments are not limited to the arrangements and instrumentality shown in the drawings.

DETAILED DESCRIPTION OF THE INVENTION

The present invention may be understood more readily by reference to the following detailed description of preferred embodiments of the invention as well as to the examples included therein. All numeric values are herein assumed to be modified by the term "about," whether or not explicitly indicated. The term "about" generally refers to a range of numbers that one of skill in the art would consider equivalent to the recited value (i.e., having the same function or result). In many instances, the term "about" may include numbers that are rounded to the nearest significant figure.

The miniblock detector described here comprises an array of silicon photomultipliers (SiPMs), which may be monolithic, discrete or multiple monolithic devices in a package, optically coupled to a block of scintillator pixels without inter-pixel reflectors ("air coupled"), or with few inter-pixel reflectors, and surrounded by a thin efficient optical reflector. Air coupling between scintillator pixels, combined with a selected surface finish, functions to control the light spread within the array of pixels via a combination of internal reflection and inter-pixel transmission. This allows optimization of event localization accomplished via segmentation of calculated position profiles. The use of inter-pixel reflectors to control light spread within the array of pixels is less desirable as light loss due to absorption by the reflector material can reduce the number of scintillation photons detected and thus degrade time and energy resolution. A drawing of one such detector block is shown in FIG. 1. Since the event scintillation light is distributed or shared within the block and the sensor array, the SiPMs are biased and the block timing is read out by a common cathode circuit, while the position and energy is read out by one of various anode readout circuits. A less efficient readout scheme requiring more fast timing channels (one for each anode) with greater power requirements and introduction of more electronic noise into the timing signal is shown in FIG. 2, while a block diagram of one possible implementation of common cathode timing readout electronics is shown in FIG. 3.

FIG. 1 is a schematic diagram of a block of air-coupled scintillator pixels (e.g. scintillator crystals) on common-cathode silicon photomultiplier light sensor array. A silicon photomultiplier light sensor 1 can be one of a j×k array with at least one of j, k>1. The active elements of the array can be individual SiPMs or part of one or more "monolithic" arrays of devices. A silicon photomultiplier array substrate 2 or circuit board can be provided to which devices are mounted. As a substrate for the devices provided by the manufacturer the substrate 2 might be ceramic or a circuit board material; the substrate 2 may contain or have mounted on the other side electronic components or may be plugged into a socket(s) or soldered onto a circuit board. A plurality of scintillator pixels 3 can be one of an m×n array of air-coupled pixels that exhibit enhanced internal reflection while still being partly optically coupled to each other. At least one of m, n>1, and, since to use the various sensor signals to determine the crystal of interaction no more sensors are necessary along an axis than there are pixels, and usually fewer are necessary, a practical detector miniblock that doesn't waste electronics channels would also have j<=n and k<=m. All these constraints make the miniblock pixelated and allow "imaging" the gamma event location by any of several known techniques such as calculating the centroid of the SiPM anode signals, and using a crystal map to identify the particular crystal event location. In general, the pixels and the sensors can be rectangular rather than square, and the entire miniblock might also be rectangular. Optical coupling 4 of scintillator pixels to silicon photomultiplier light sensors might comprise only an optical coupling material, i.e. the pixels are bonded directly to the silicon sensor dies, or more likely an optical window is bonded to the array of silicon photomultipliers and the scintillator pixels are bonded and coupled to the window, or additionally, though it can degrade timing performance, a "light-guide"—or just a thicker window—may be used, which spreads light to aid in the "imaging" and separation of events in pixels processed/calculated from the anode signals. The array of scintillator pixels 3 is wrapped by an external reflector material 5.

Figure 2:
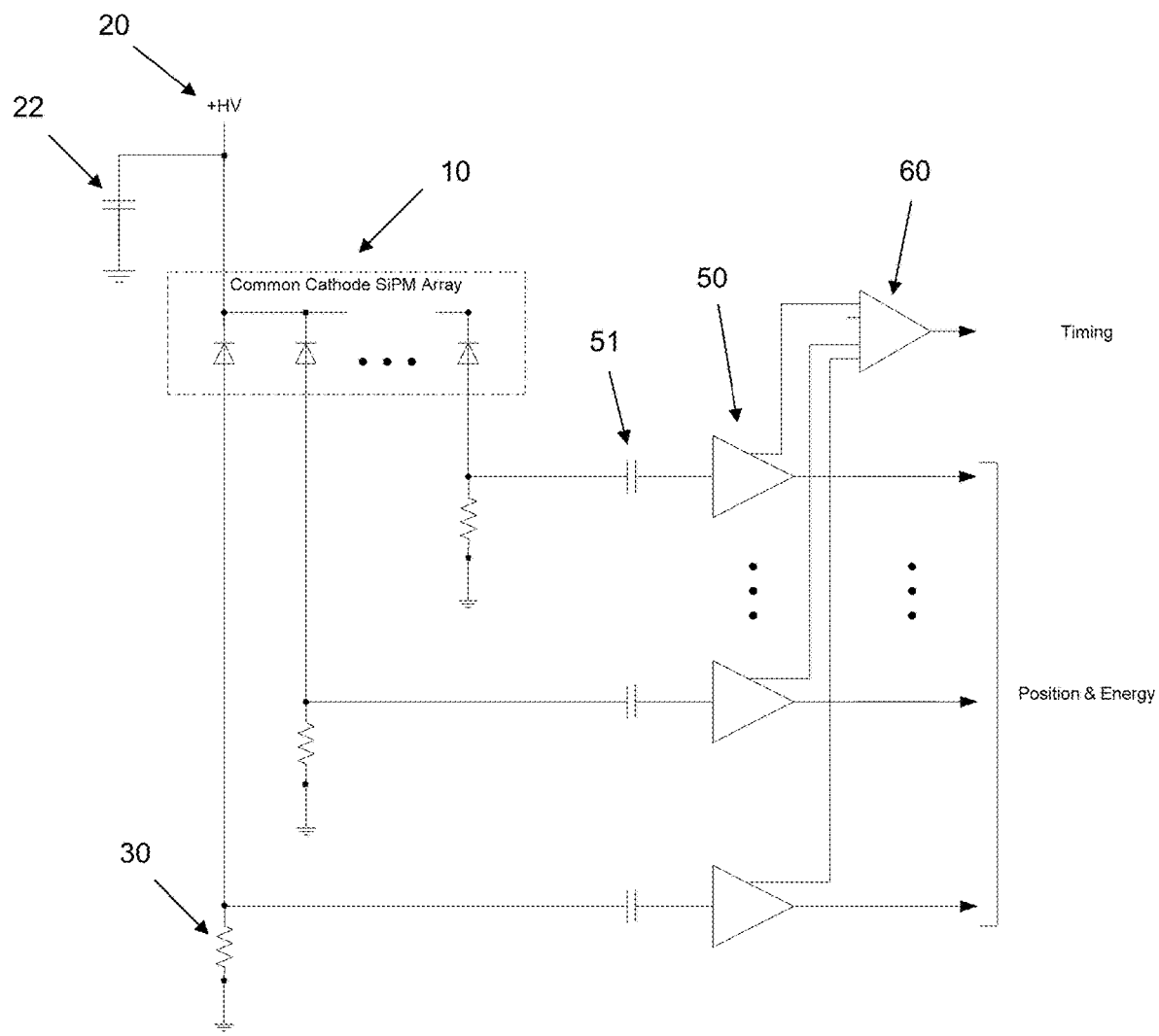
FIG. 2: is a schematic showing implementation of timing signal generation from the sum of anode signals.

FIG. 2 is a schematic showing implementation of timing signal generation from the sum of anode signals. A silicon photomultiplier sensor array 10 with common cathode connection can be coupled to a high voltage bias supply 20, having a power supply bypass capacitor 22. An anode load resistor 30 can be provided for each sensor in the silicon photomultiplier sensor array 10. An anode preamplifier 50, with timing and energy outputs, can be provided for each sensor in the silicon photomultiplier sensor array 10. An anode preamplifier coupling capacitor 51 can be provided for each sensor in the silicon photomultiplier sensor array 10. A summing amplifier 60 can be provided for timing channel signal generation.

Figure 3:
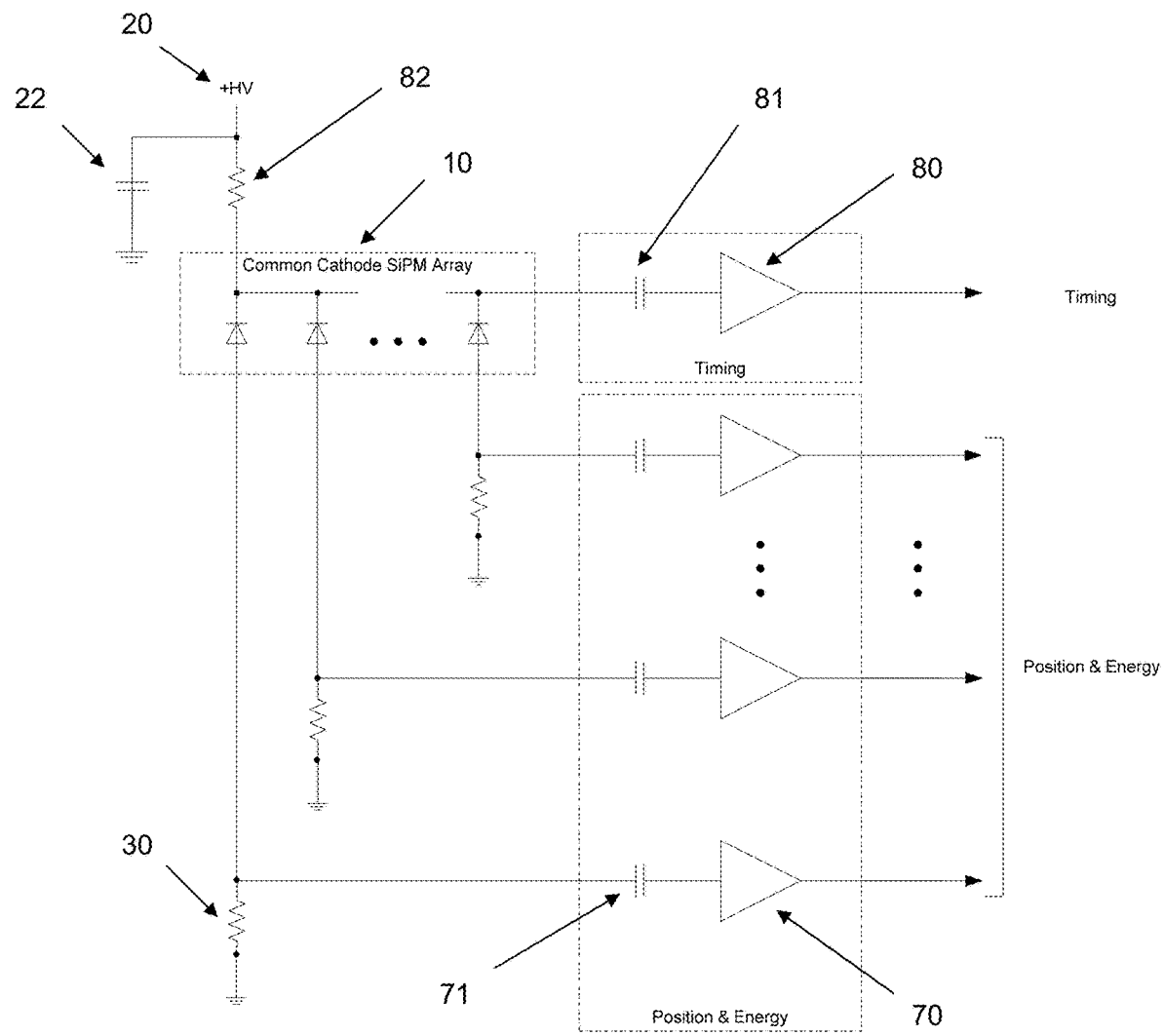
FIG. 3: is a schematic showing implementation of timing signal generation from the common cathode signal.

FIG. 3 is a schematic showing implementation of timing signal generation from the common cathode signal. A silicon photomultiplier sensor array 10 with common cathode connection can be coupled with a high voltage bias supply 20, having a power supply bypass capacitor 22. An anode load resistor 30 can be provided for each sensor in the silicon photomultiplier sensor array 10. An anode energy preamplifier 70 can be provided for each sensor in the silicon photomultiplier sensor array 10. An anode preamplifier coupling capacitor 71 can be provided for each sensor in the silicon photomultiplier sensor array 10. A cathode timing preamplifier 80 can be provided. A cathode preamplifier coupling capacitor 81, which blocks the high voltage cathode bias potential, and cathode bias resistor 82 can be provided for generating cathode timing signal pickoff.

There are several significant advantages to the common-cathode timing approach. The most important of these are reductions in system complexity and power requirements. The number of timing channels, that is fast preamplifiers and discriminators, is reduced by an order of magnitude over the anode sum method—the exact reduction obviously depends on the block SiPM array dimensions, but a factor of 9 or even 16 or more is likely. In addition, since the bandwidth required of the anode preamplifiers is dramatically reduced, their preamplifiers can be expected to each require much less power. Furthermore, it is possible to reduce the number of channels to be digitized for energy and position calculation (by analog processing into, for example, A,B,C, and D signals analogous to PMT block detector signals or positions X,Y and energy E signals) thus reducing the number of analog to digital converters (ADCs) required and also reducing the demands on field programmable gate arrays (FPGAs) performing subsequent digital processing such as energy determination and correction, crystal identification and time walk correction.

Another important advantage of the common-cathode timing approach is that the cathode timing and anode position/energy channels may be separately optimized for their intended use. These optimizations include frequency bandwidth selection, amplifier topologies employed, and specific technologies chosen for any integrated circuit implementation. For example, the timing channel can employ a saturated amplifier without the need to retain energy information, while the anode signals can be filtered and shaped at much lower bandwidth to enable use of very low power, low speed ADCs. The actual time of an event relative to the system timebase can be determined by various methods, such as discriminator and time to digital converter (TDC) methods, digital timing computations based on continuous digitization of the amplified and filtered timing signal, or others.

Finally, the common-cathode timing approach increases flexibility for potential multiple systems designs. For example, the cathode timing channel implementation may be handled differently in an MR-compatible detector design than in one for a conventional PET-CT system, while an ASIC for analog processing of the numerous lower bandwidth anode channels could be used for both systems. Alternatively, since the common-cathode approach is somewhat independent of the specific SiPM array dimensions and the number of SiPM sensors required within a particular block design, the same timing implementation might be paired with different anode channel ASICs in different systems. Also, the same basic approach can be used regardless of the specifics of sensor array fabrication and packaging. This allows the freedom to choose arrays of discrete devices, a single monolithic common cathode array, or an assembly of monolithic common cathode arrays, optimizing cost and reliability, even as suppliers and their cost/performance capabilities change, without fundamentally changing the critical timing implementation chosen.

Physically, the detector block design can be adapted to different small scintillator pixel arrays with differently sized pixels (typically ~2 to ~4 mm square) in differently dimensioned arrays (3×3 to 8×8 or larger), and SiPM sensor sizes (typically 3 to 6 mm square) and array dimensions (3×3, 4×4, and larger). Experiments and simulations suggest excellent timing with chemically etched LSO scintillator (~38,000 ph/MeV, ~40 ns decay time) on the order of 250 ps or better coincidence resolving time (CRT) can be achieved for blocks of 12, 16 or even over 20 mm square. These physical sizes provide sufficient photopeak sensitivity through 511 keV gamma absorption within the block to outperform a 1:1 coupled scheme when the Figure of Merit of estimated signal to noise ratio, proportional to sqrt (sensitivity) and inversely proportional to sqrt(CRT) is considered. (Conti et. al.)

Figure 4:
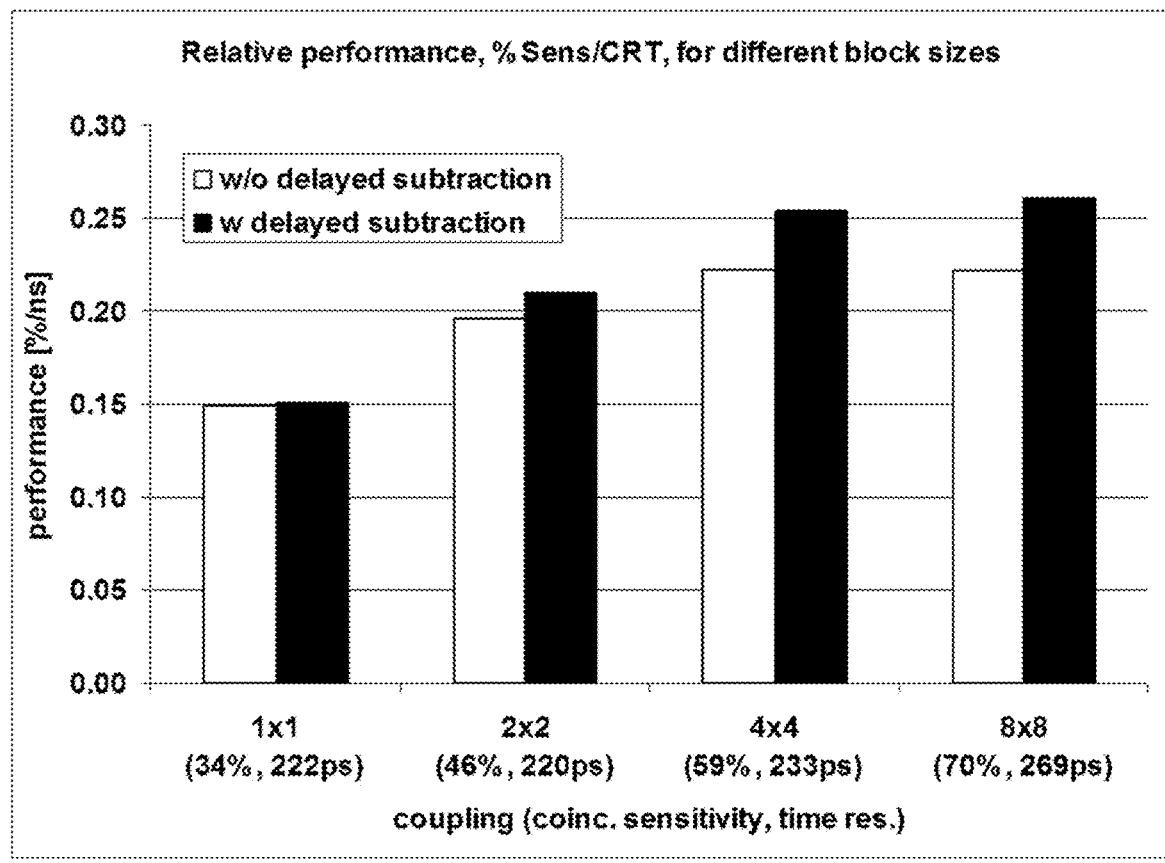
FIG. 4: is a chart showing Monte Carlo simulation results showing nearly 1:1 coupled case timing and significantly better Figure of Merit for a 4×4 small block of 4×4×20 mm LSO crystals coupled to a 4×4 channel 4 mm SiPM array.

To estimate what the performance of the envisioned detector could be, a comprehensive Monte Carlo simulation of the detector was implemented. The simulation covers the interactions of the 511 keV photons with the scintillator material, the optical path of the generated scintillation light, the SiPMs modeled from manufacturer specifications and measurements, and readout electronics based on a measured response function and SPICE modeling of amplified signal behavior for larger array sizes. Various 4×4×20 mm pixel array sizes, from 1×1 to 8×8, were simulated at ideal 100% fill factor optical coupling to the modeled and experimentally tested SiPMs in corresponding optically coupled arrays. Air-coupled 3M ESR, that is used without optical adhesive, which has been experimentally determined to be almost as effective as multiple layers of expanded Teflon reflector material, was simulated as the external reflector. Gamma irradiation was homogeneous, perpendicular to the face of the detectors, and photopeak sensitivity as a percentage of irradiation was calculated in each case. When combined with estimated timing at the optimum leading edge timing threshold, these simulations suggest that a 16 mm square or possibly somewhat larger block employing common cathode time pickoff would provide the best overall performance, as shown in FIG. 4. FIG. 4 is a chart showing Monte Carlo simulation results showing nearly 1:1 coupled case timing and significantly better Figure of Merit for 4×4 small block of 4×4×20 mm LSO crystals coupled to 4×4 channel 4 mm SiPM array.

Several experiments testing the effects of the light-sharing block with SiPM array concept and the performance of the common-cathode timing method have been performed using Hamamatsu 50 μm microcell size SiPM (identified by Hamamatsu as a multi-pixel photon counter, or MPPC), both single devices and monolithic 12 mm square arrays. Arrays were wrapped in four layers of 254 μm thick Tetratex expanded PTFE, while no reflector was placed between pixels of arrays. These experiments are consistent with the previously described Monte Carlo simulations.

Timing was measured against a calibrated single PMT/LSO crystal reference. All timing values presented here are estimated coincidence resolving times (CRTs), computed by "unfolding" the single-sided timing reference value and multiplying by √2, i.e. under the assumption that the timing uncertainties are normally distributed and thus add in quadrature. Timings are derived from digitized data and presented using leading edge thresholds on crystal photopeak events (approximately 430 keV to 650 keV), and are either uncorrected, or corrected with a digital delayed subtraction method (Piemonte et. al.—see FIG. 5) to remove baseline variation and dark count baseline noise effects, followed by energy normalization walk correction (see FIG. 6). An analog pulse shaping technique suitable for ASIC implementation employing pole-zero compensation could be used in a system without high speed analog to digital conversion of the timing signal, as reported in Gola et. al. Other methods of filtering to obtain optimum timing performance for specific SiPM array cases are also possible.

Figure 5:
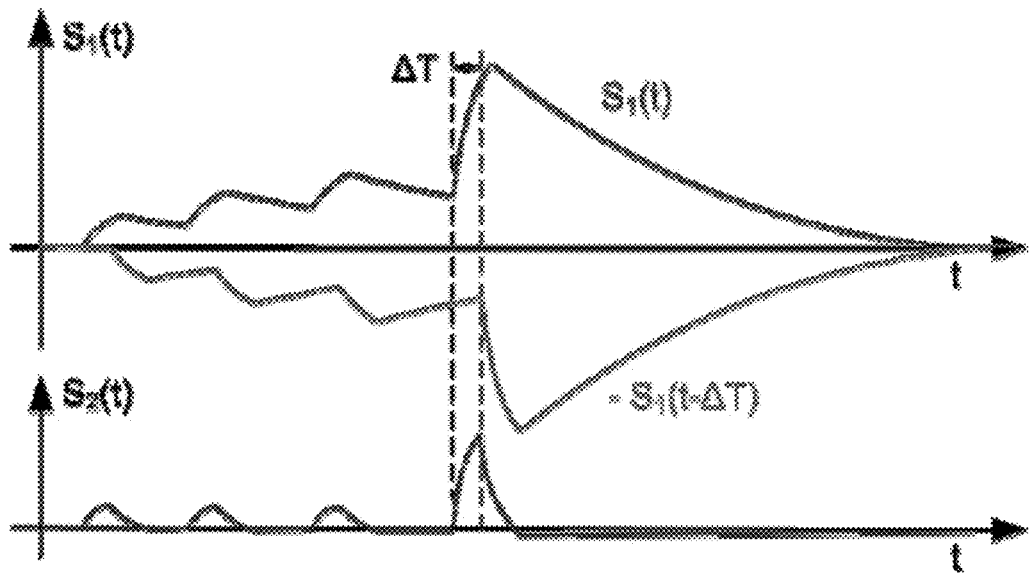
FIG. 5: is a schematic representation of a method from Piemonte, et. al. explaining the digital delayed subtraction algorithm; the SiPM signal is $S_1(t)$: a delayed and inverted replica of the signal is summed to itself, obtaining the filtered signal $S_2(t)$, which is fed to a traditional leading edge discriminator.

FIG. 5 is a schematic representation of a method from Piemonte, et. al. explaining the digital delayed subtraction algorithm; the SiPM signal is $S_1(t)$: a delayed and inverted replica of the signal is summed to itself, obtaining the filtered signal $S_2(t)$, which is fed to a traditional leading edge discriminator. Baseline deviation due to dark noise pulses, the length of the processed pulse and equivalently the effective noise due to the dark pulses is reduced which improves timing performance for scintillation events.

Figure 6A:
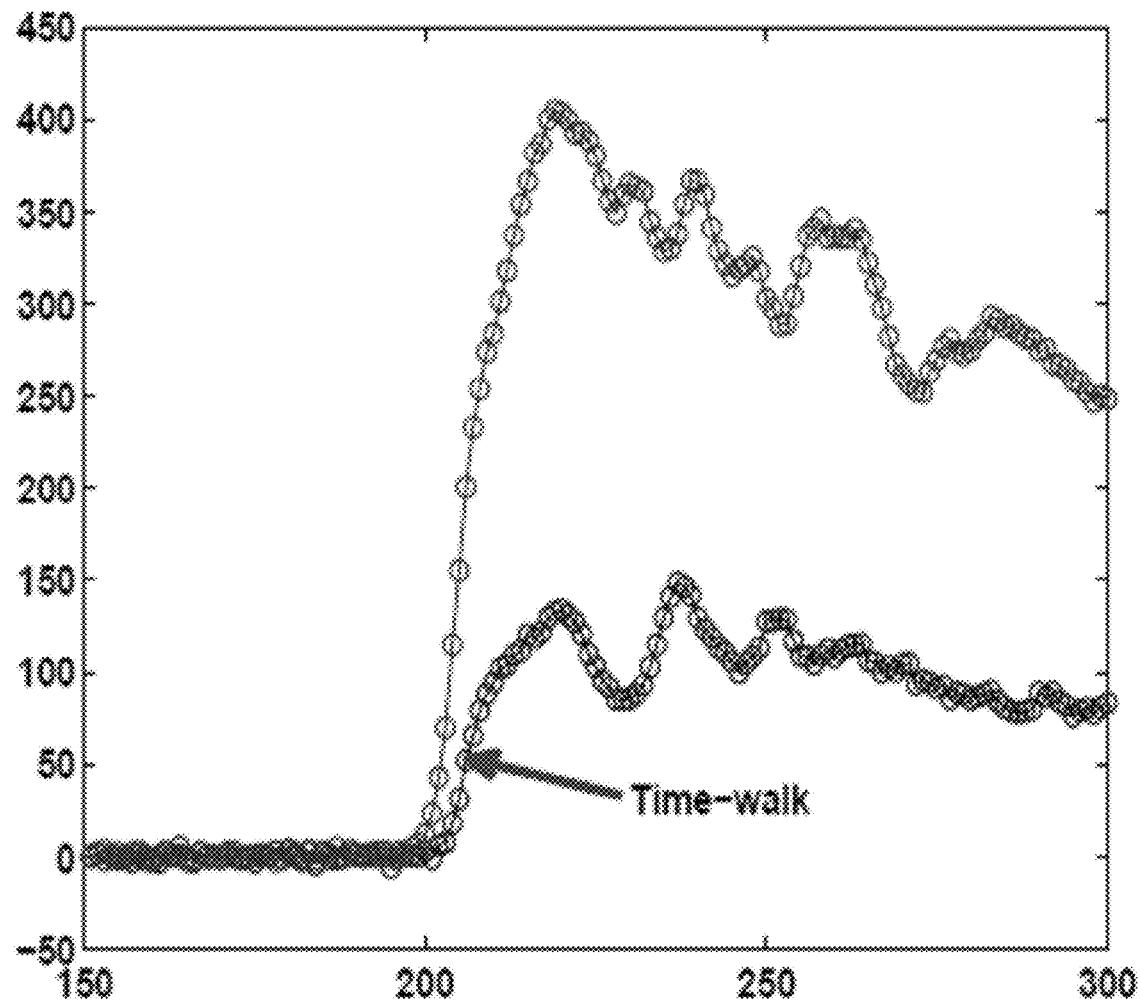
FIG. 6A: is a chart showing the need for an energy normalization based time-walk correction method, specifically the large difference in trigger time without energy normalization

FIG. 6A is a chart showing the need for an energy normalization based time-walk correction method, specifically the large difference in trigger time without energy normalization.

Figure 6B:
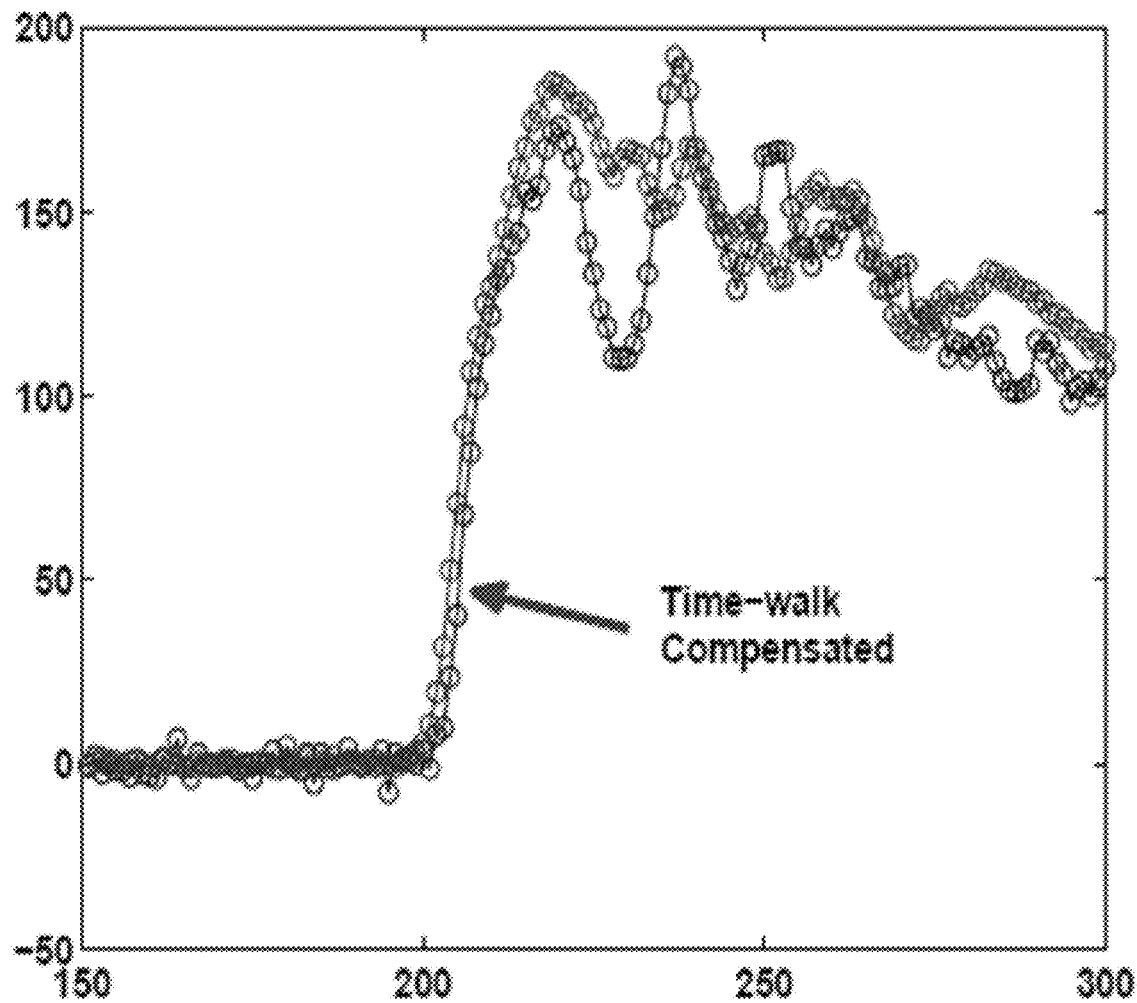
FIG. 6B: is a chart showing an energy normalization based time-walk correction method, relative to FIG. 6A.

FIG. 6B is a chart showing the concept of an energy normalization based time-walk correction method; relative to FIG. 6A, FIG. 6B shows a much smaller difference in trigger time when using energy normalization techniques.

Figure 7:
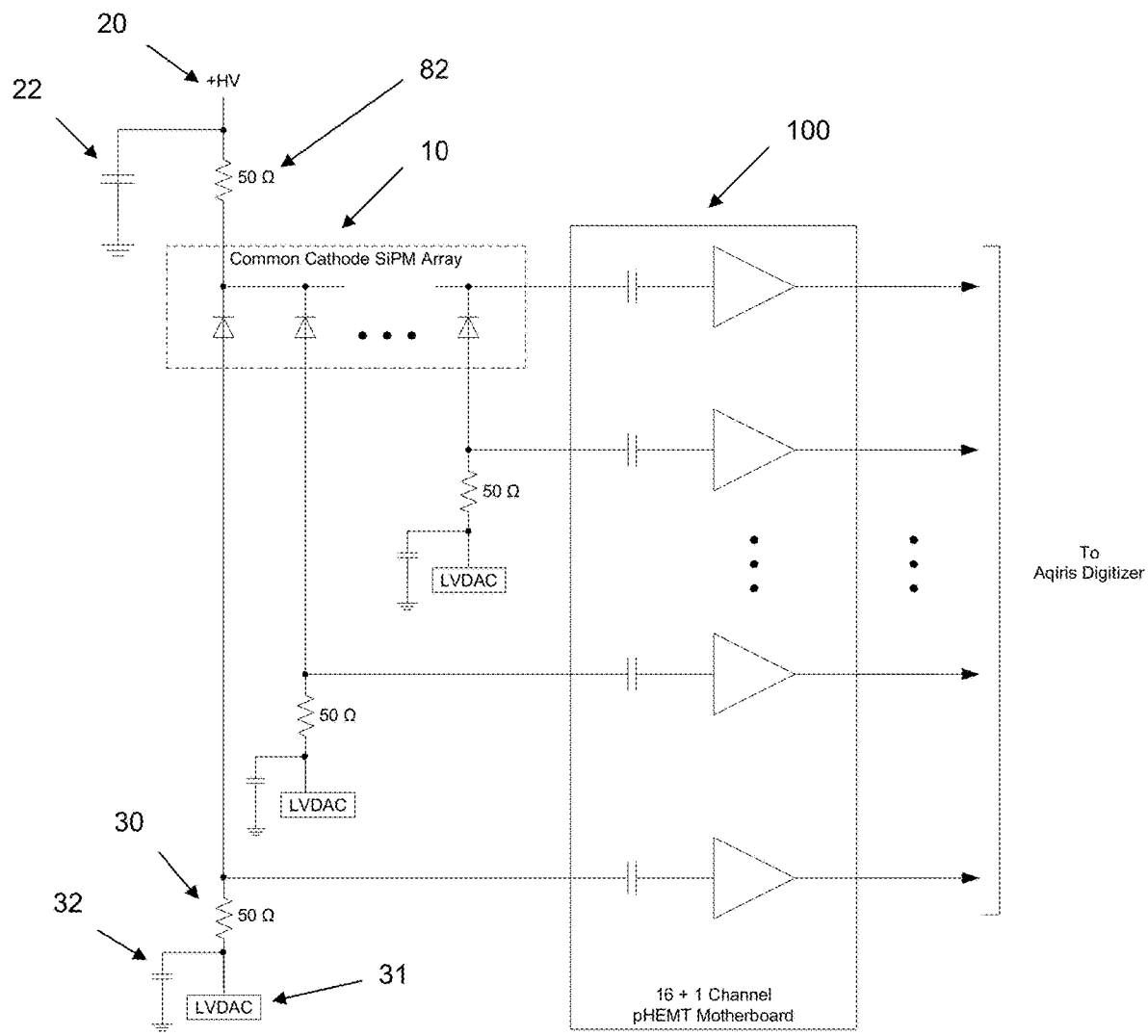
FIG. 7: is a schematic of a 16+1 channel pHEMT RF amplifier R&D system.

The electronics used in experiments were a 17 channel low noise pHEMT RF amplifier board shown in FIG. 7 with data acquisition via a 20 channel, 2 Gsample per second, 10 bit Agilent Acqiris system and custom software. Data were processed with custom Matlab code. Load resistors used on the cathode and anode channels match the 50Ω transmission line impedances used in the system design, but do not represent an optimized implementation. In addition, the 120 pF coupling capacitors were chosen during some timing optimization studies, and do not necessarily achieve the best timing for this configuration. Low voltages using a multi-channel digital to analog converter (DAC) were separately controlled to set individual SiPM operating voltages, at the same voltage over breakdown for all array devices (determined relative to those specified in Hamamatsu provided data), or at various different voltages to test operating voltage tolerance effects. Unless otherwise noted, devices were operated at a bias voltage 0.7 V above Hamamatsu's specified $V_{op}$, at which the device gains are almost exactly $7.5 \times 10^5$.

FIG. 7 is a schematic of the 16+1 channel pHEMT amplifier R&D system. A silicon photomultiplier sensor array 10 with common cathode connection can be coupled to a high voltage bias supply 20, having a power supply bypass capacitor 22. An anode load resistor 30 can be provided for each sensor in the silicon photomultiplier sensor array 10. A low voltage digital to analog converter (LVDAC) output 31 can be provided for individual anode gain control. A bypass capacitor 32 can be provided for each low voltage digital to analog converter. A cathode bias resistor 82 can be provided for generating cathode timing signal pickoff. A custom 16+1 channel capacitively-coupled high bandwidth preamplifier board 100 can be provided for cathode and anode signal amplification.

Figure 8A:
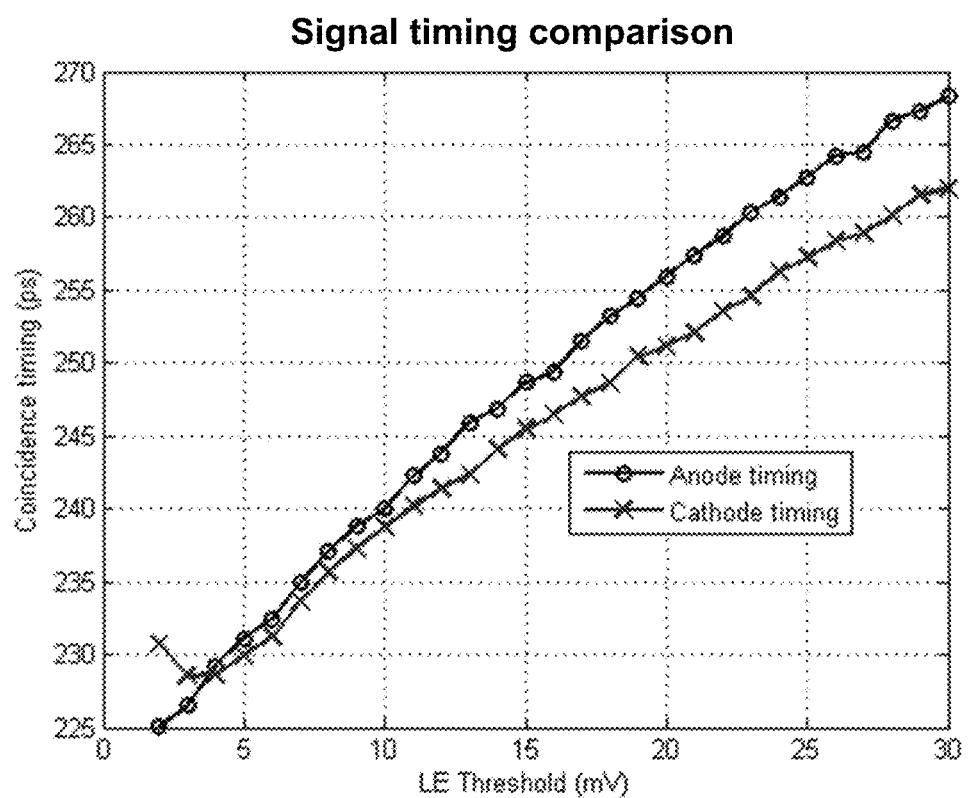
FIG. 8A: is a chart showing the timing performance comparison for simultaneous anode and cathode signal pickoff, for a single 3×3×20 mm LSO pixel on a discrete 3 mm square SiPM.
Figure 8B:
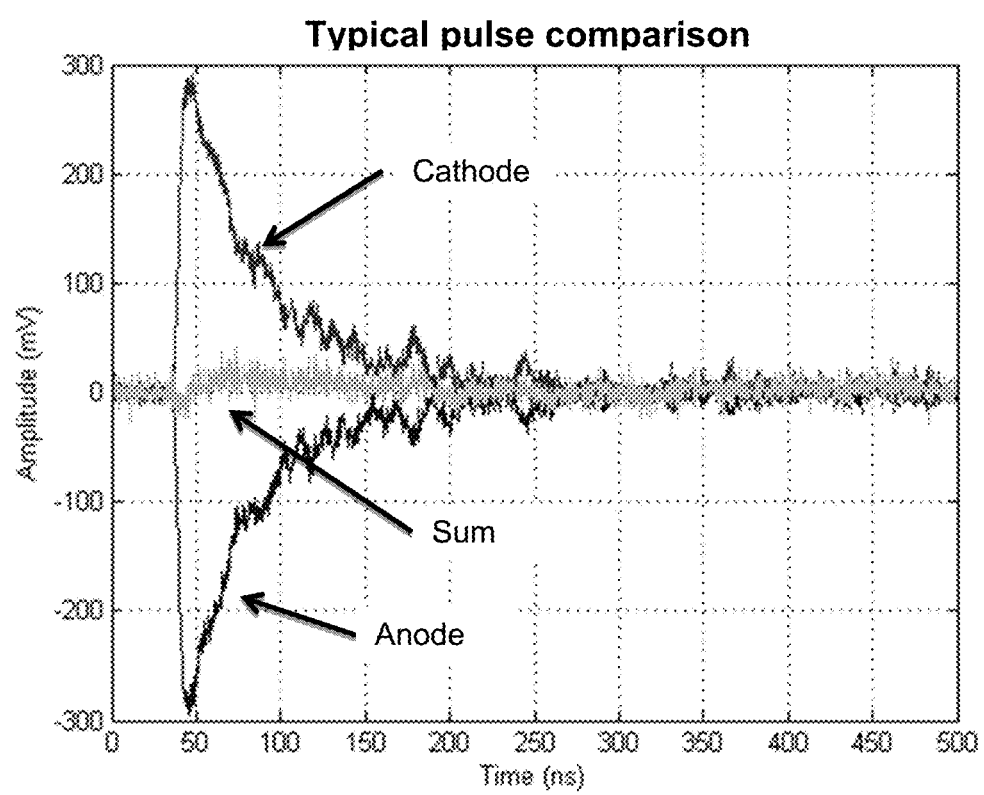
FIG. 8B: is a chart showing the typical 511 keV photopeak LSO pulse comparison for simultaneous anode and cathode signal pickoff, for a single 3×3×20 mm LSO pixel on a discrete 3 mm square SiPM.

FIG. 8A is a chart showing the timing performance comparison for simultaneous anode and cathode signal pickoff, for a single 3×3×20 mm LSO scintillator pixel on a discrete 3 mm square SiPM. FIG. 8B is a chart showing the typical 511 keV photopeak LSO pulse comparison for simultaneous anode and cathode signal pickoff, for a single 3×3×20 mm LSO pixel on a discrete 3 mm square SiPM. FIG. 8 shows the results of simultaneous anode and cathode signal pickoff on our test system for a single crystal on a discrete Hamamatsu 3 mm square, 50 μm microcell SiPM. Anode and cathode signals are virtually identical (though of opposite polarity), and timing performance is comparable. The device used in this test had a very low dark count rate (~0.5 Mcps at Hamamatsu's specified $V_{op}$).

Figure 9A:
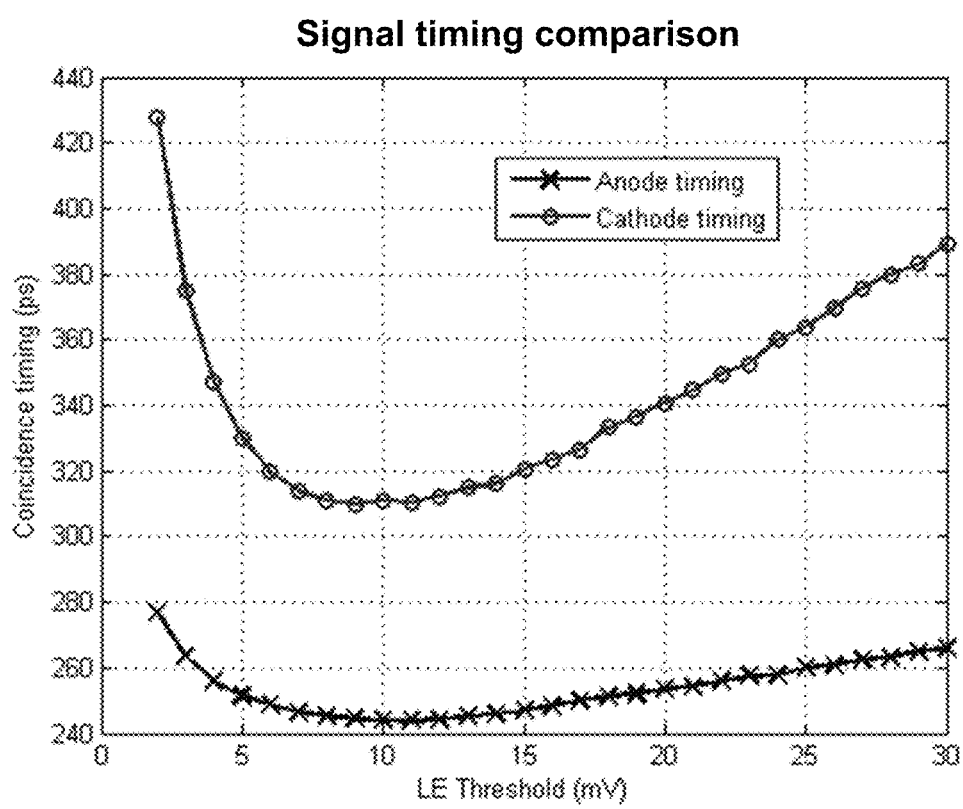
FIG. 9A: is a chart showing the timing performance comparison for simultaneous anode and cathode signal pickoff, for a single 3×3×20 mm LSO pixel on a 4×4 channel monolithic array of 3 mm square SiPMs.
Figure 9B:
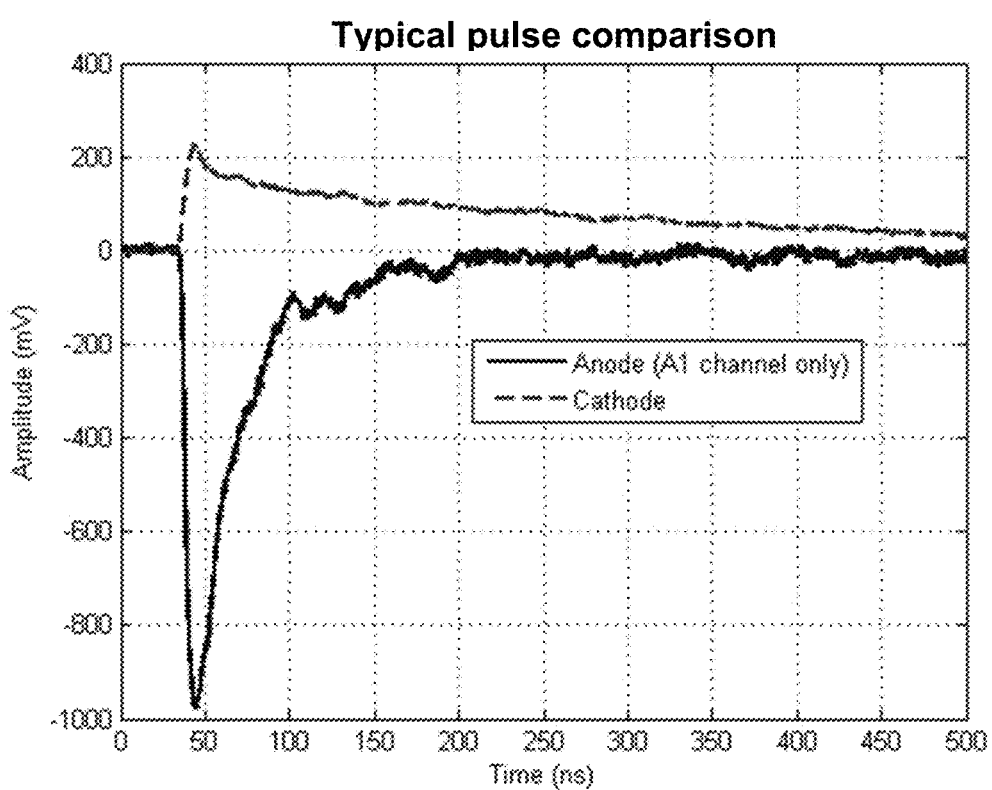
FIG. 9B: is a chart showing the typical 511 keV photopeak LSO pulse comparison for simultaneous anode and cathode signal pickoff, for a single 3×3×20 mm LSO pixel on a 4×4 channel monolithic array of 3 mm square SiPMs.

FIG. 9A is a chart showing the timing performance comparison for simultaneous anode and cathode signal pickoff, for a single 3×3×20 mm LSO scintillator pixel on a 4×4 channel monolithic array of 3 mm square SiPMs. FIG. 9B is a chart showing a typical 511 keV photopeak LSO pulse comparison for simultaneous anode and cathode signal pickoff, for a single 3×3×20 mm LSO scintillator pixel on a 4×4 channel monolithic array of 3 mm square SiPMs.

Timing performance and typical anode and cathode pulses for the same crystal on a 4×4 channel 3 mm square monolithic SiPM array are shown in FIG. 9. This array had a very high dark count rate (>12 Mcps per SiPM), and the cathode timing, without baseline correction methods, is thus substantially degraded relative to the single SiPM anode timing, as the cathode signal contains the noise from all 16 devices. The anode timing is somewhat worse than that obtained on the single device, due to the much higher dark count rate, and possibly also due to some additional light loss in the larger window of the array package.

The typical pulse comparison in FIG. 9B shows important effects on the timing signal derived from the common cathode of an array of SiPMs. First, we see that the pulse has a much longer "tail," i.e. decay time, due to the larger total capacitance of the entire array (# devices×$C_d$); the LSO decay time is extended by the time constant of the circuit, approximately the total array C×the preamplifier $R_{in}$. Also we can see that though the rise time of the cathode signal is not degraded, due to the charge supplied by all neighboring devices the peak cathode signal level is decreased.

Figure 10A:
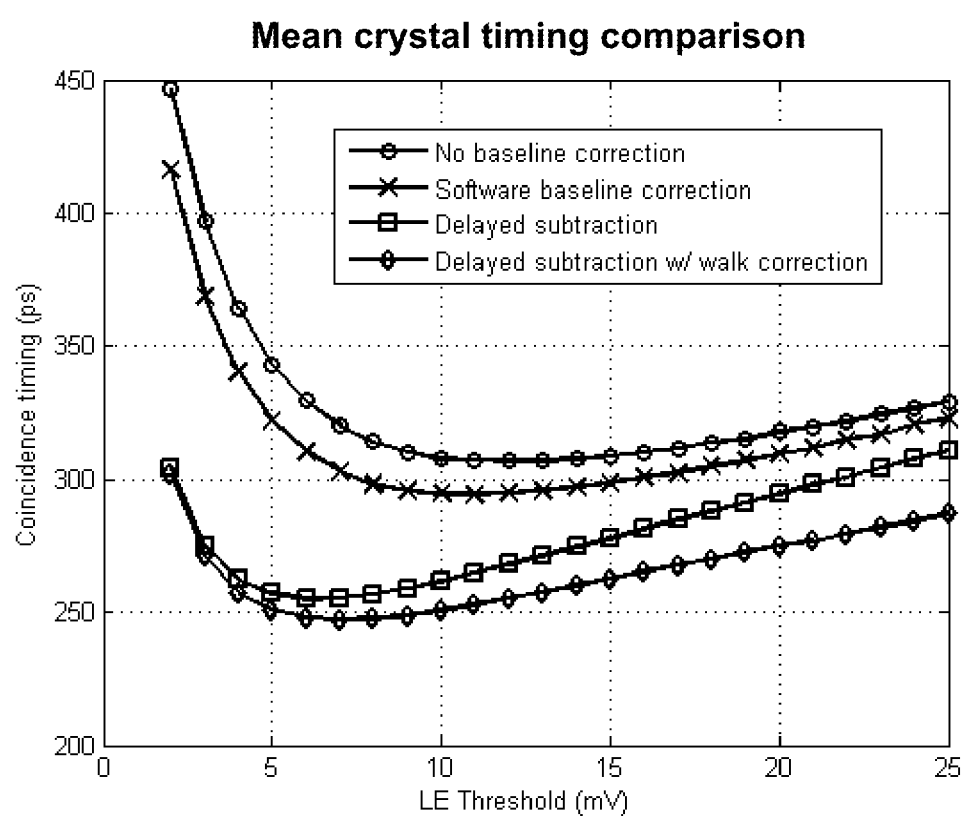
FIG. 10A: is a chart showing mean crystal timing performance for simultaneous anode and cathode signal pickoff, with and without various digital corrections, for a 4×4 3×3×20 mm LSO crystal array on a 4×4 channel monolithic array of 3 mm square SiPMs.
Figure 10B:
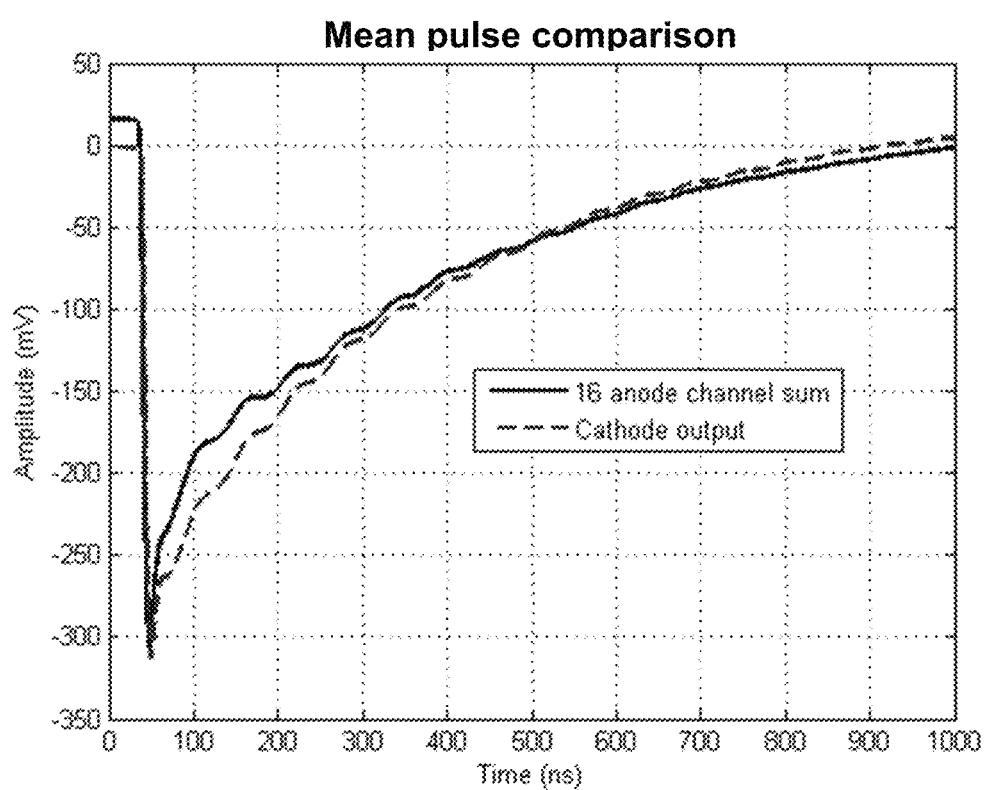
FIG. 10B: is a chart showing mean 511 keV photopeak LSO pulses, comparing cathode and anode-sum pulses, for simultaneous anode and cathode signal pickoff, for a 4×4 3×3×20 mm LSO crystal array on a 4×4 channel monolithic array of 3 mm square SiPMs.

FIG. 10A is a chart showing mean crystal timing performance for simultaneous anode and cathode signal pickoff, with and without various digital corrections, for a 4×4 array of 3×3×20 mm LSO crystals on a 4×4 channel monolithic array of 3 mm square SiPMs. FIG. 10B is a chart showing mean 511 keV photopeak LSO pulses, comparing and showing the similarity of cathode and anode-sum pulses, for simultaneous anode and cathode signal pickoff, for a 4×4 array of 3×3×20 mm LSO crystals on a 4×4 channel monolithic array of 3 mm square SiPMs. FIG. 10 shows mean crystal cathode timing results for a 4×4 scintillator pixel array on the same monolithic SiPM array as used for the data represented in FIG. 9. Individual crystal timing curves were computed from events separated via the position profile shown in FIG. 11. Here we see that digital delayed subtraction baseline correction along with additional timing walk correction allows recovery of a substantial amount of the timing resolution lost due to the very high total dark count rate of this SiPM array (~200 Mcps total).

Figure 11:
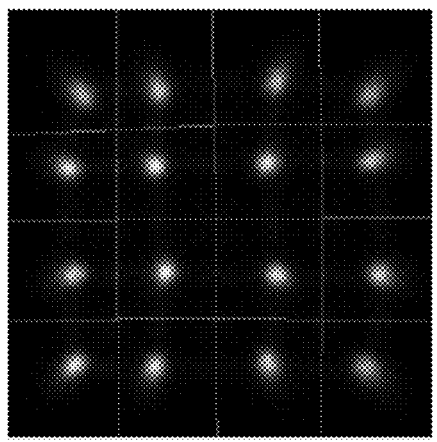
FIG. 11: is a diagram showing position profile and calculated crystal regions map for the 4×4 3×3×20 mm LSO crystal array on a 4×4 channel monolithic array of 3 mm square SiPMs.

FIG. 11 is a diagram showing the position profile and calculated crystal regions map for a 4×4 array of 3×3×20 mm LSO crystals on a 4×4 channel monolithic array of 3 mm square SiPMs. Event locations within the scintillator pixel array, that is in the various crystals, are easily determined by standard methods.

Figure 12A:
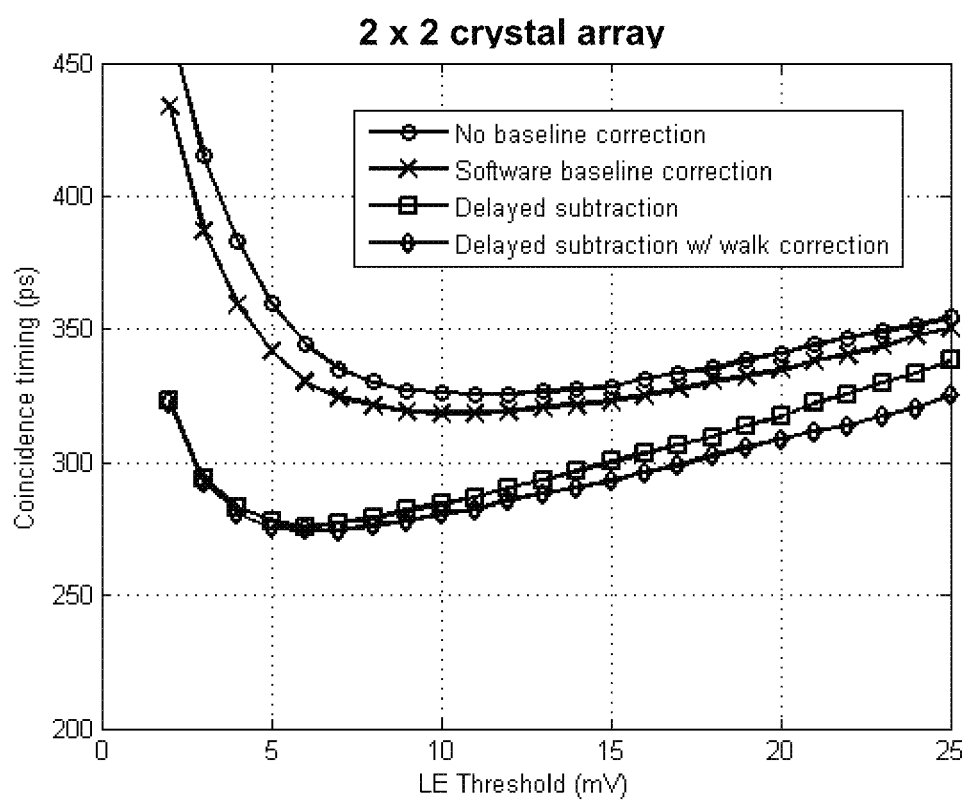
FIG. 12A: is a chart showing a comparison of mean crystal timing for 2×2 3×3×20 mm LSO crystal arrays on the high dark count rate monolithic 4×4 SiPM array.
Figure 12B:
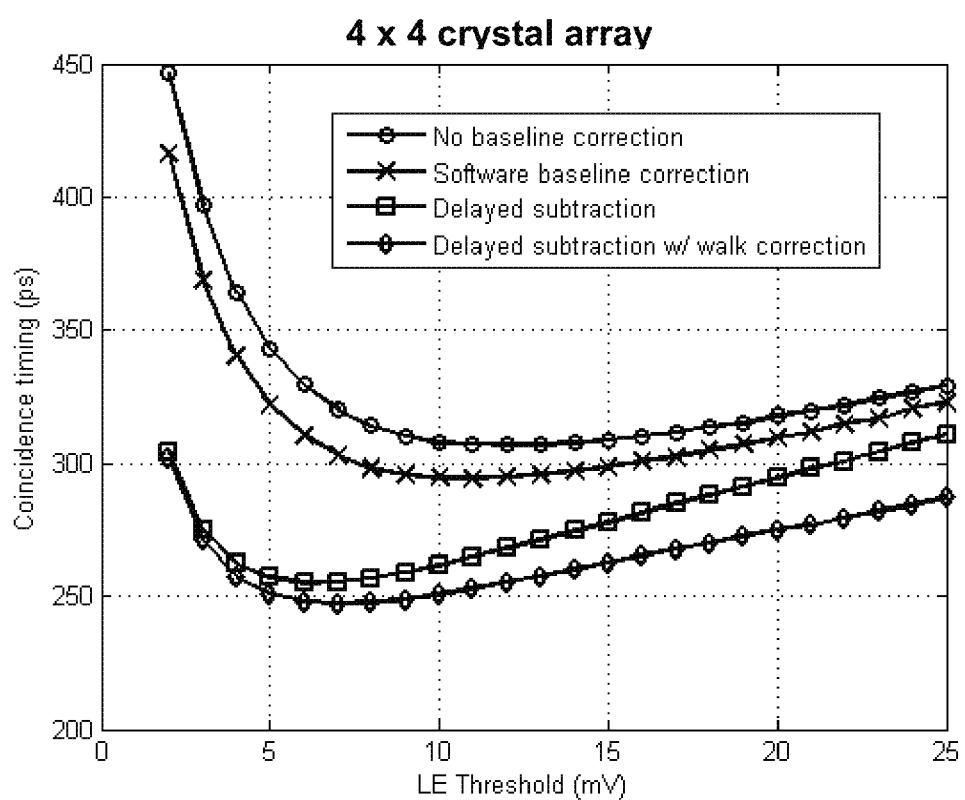
FIG. 12B: is a chart showing a comparison of mean crystal timing for 4×4 3×3×20 mm LSO crystal arrays on the high dark count rate monolithic 4×4 SiPM array.

FIG. 12A is a chart showing a comparison of mean crystal timing for a 2×2 array of 3×3×20 mm LSO crystals on the high dark count rate monolithic 4×4 SiPM array. FIG. 12B is a chart showing a comparison of mean crystal timing for a 4×4 array of 3×3×20 mm LSO crystals on the high dark count rate monolithic 4×4 SiPM array. FIG. 12 shows the timing improvement resulting from better light collection in blocks of intermediate size. Since we have been limited to using 12 mm×12 mm sized SiPM arrays, we do not have experimental results for larger arrays of scintillator pixels. However, optical/SiPM model Monte Carlo simulations suggest that favorable timing performance can be achieved with at least 20 mm×20 mm arrays, using currently available worst-case dark count rate devices (2 Mcps per 3 mm device).

Figure 13A:
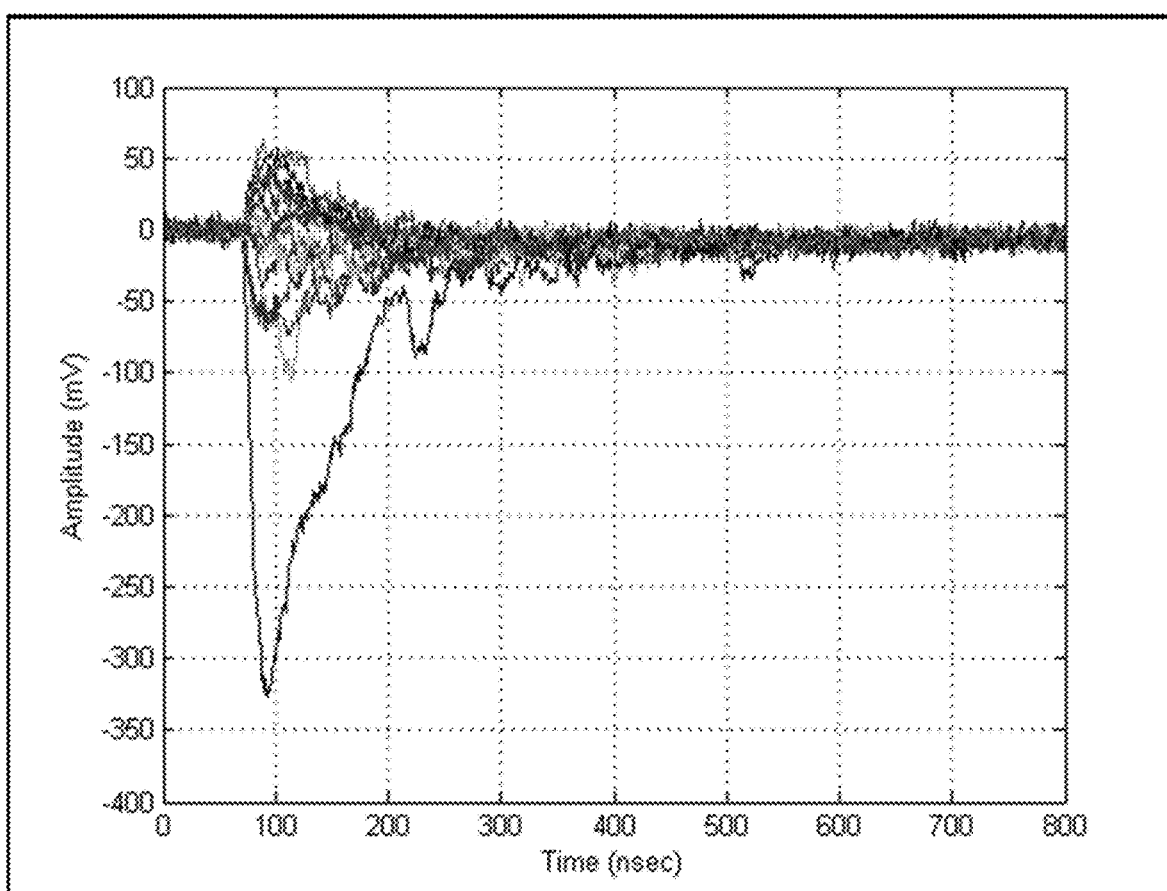
FIG. 13A: is a chart showing the effect of charge sharing on anode signals, specifically opposite polarity signals due to shared-charge current flow.
Figure 13B:
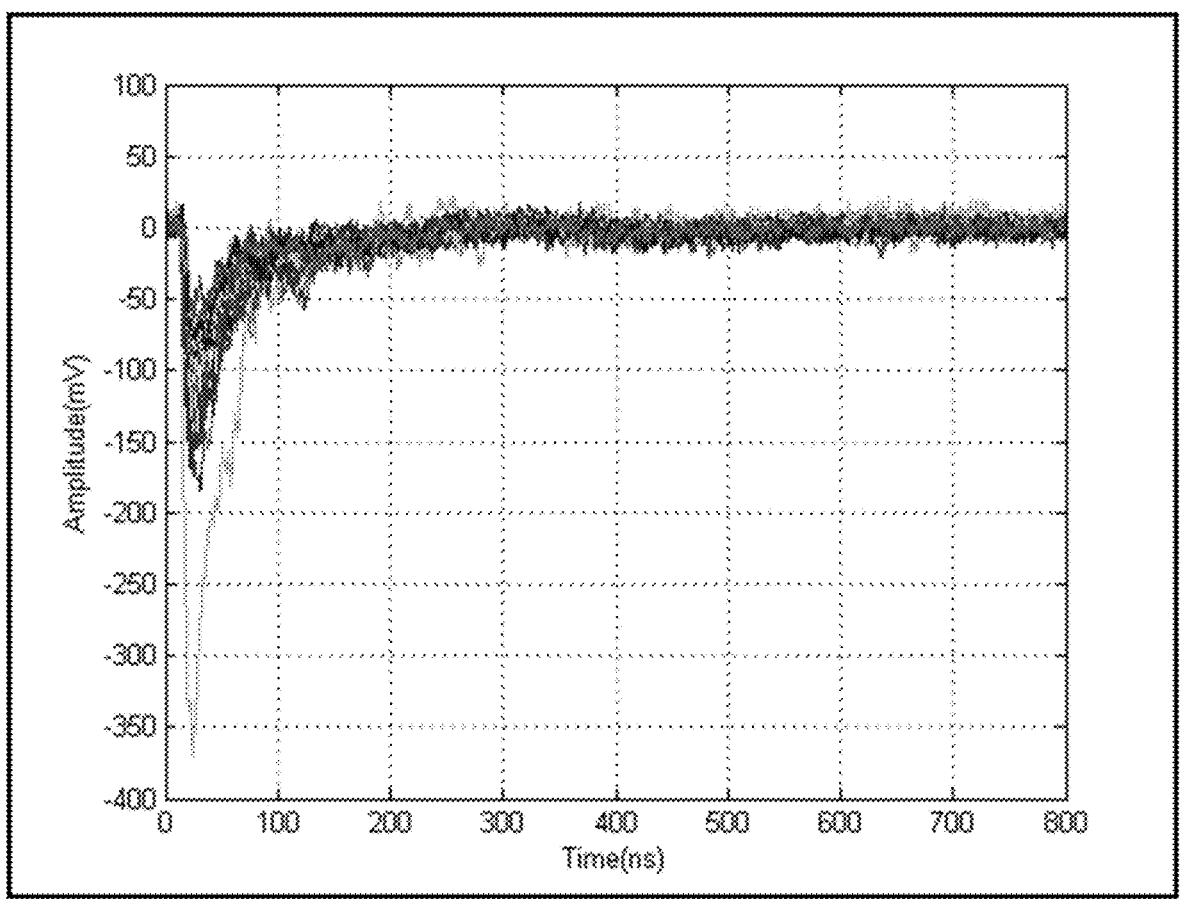
FIG. 13B: is a chart showing the effect of charge sharing on anode signals, specifically that constant bias voltage provided to the common cathode without signal pickoff shows no such effect.

FIG. 13A is a chart showing the effect of charge sharing on anode signals, specifically opposite polarity signals due to shared-charge current flow. FIG. 13B is a chart showing the effect of charge sharing on anode signals, specifically that constant bias voltage provided to the common cathode without signal pickoff shows no such effect. When the common-cathode signal is read out by the 50Ω input impedance voltage preamplifiers employed in these experiments, charge supplied to the SiPM(s) in breakdown comes partially from neighboring devices. The current flowing in these devices produces signals of opposite polarity in their anode voltage readout circuits. However, when used in position and energy calculations, integrated values acquired from these signals has been seen to produce excellent position profiles and event localization as well as accurate energy spectra after correction for SiPM non-linearity.

Figure 14A:
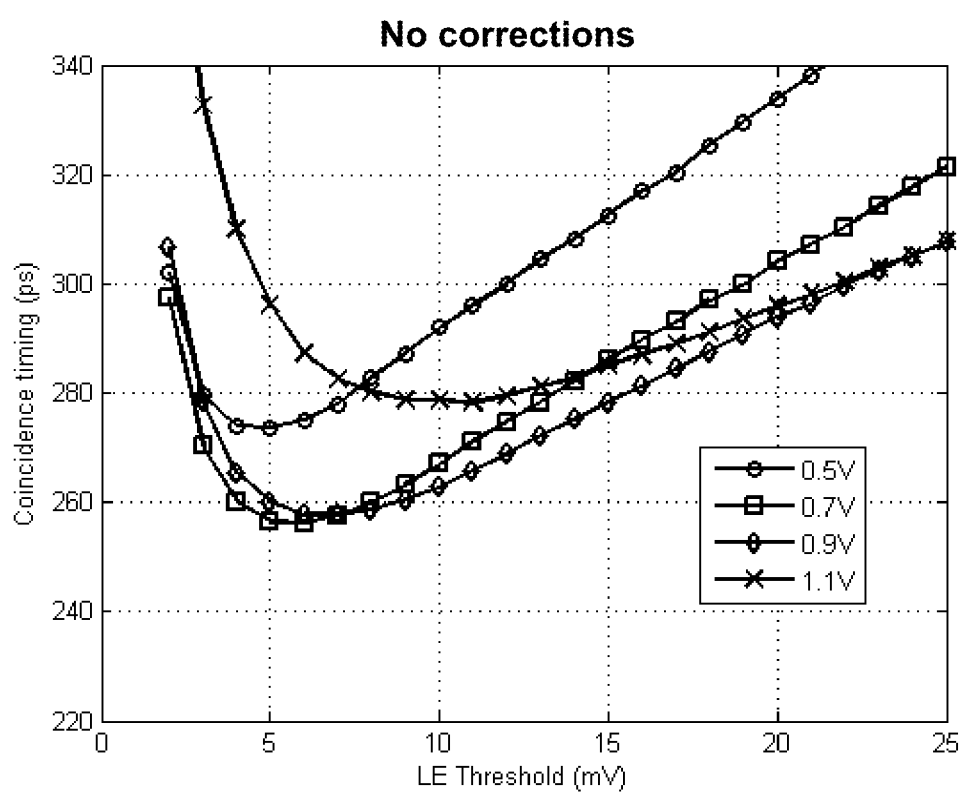
FIG. 14A: is a chart showing timing results at various over-voltages with an array of 4×4×20 mm crystals on a low dark count rate 3×3 channel 4 mm monolithic SiPM array with no corrections.
Figure 14B:
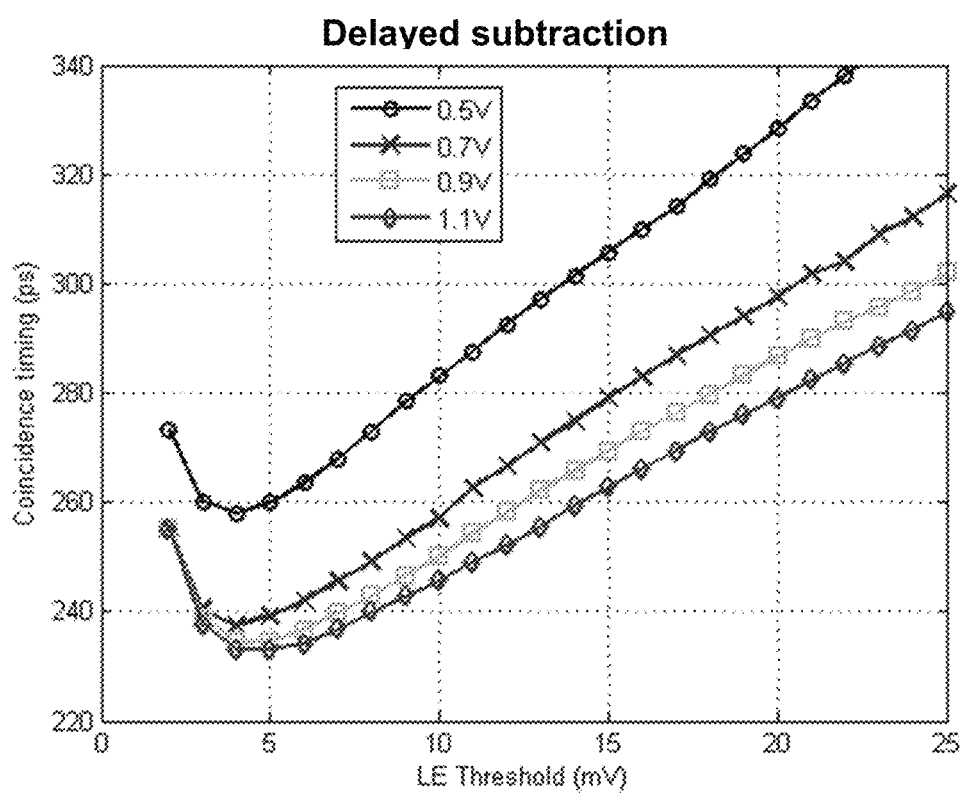
FIG. 14B: is a chart showing timing results at various over-voltages with an array of 4×4×20 mm crystals on a low dark count rate 3×3 channel 4 mm monolithic SiPM array with delayed subtraction.
Figure 14C:
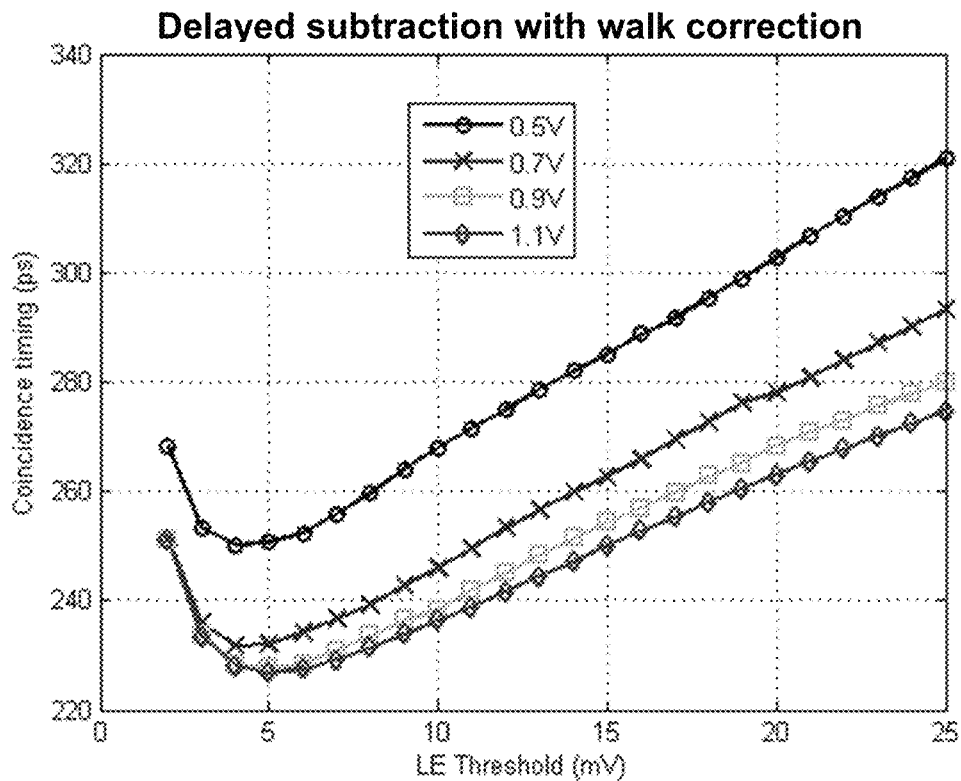
FIG. 14C: is a chart showing timing results at various over-voltages with an array of 4×4×20 mm crystals on a low dark count rate 3×3 channel 4 mm monolithic SiPM array with delayed subtraction with time walk correction.

FIG. 14A is a chart showing timing results at various over-voltages with an array of 4×4×20 mm crystals on a low dark count rate 3×3 channel 4 mm monolithic SiPM array with no corrections. FIG. 14B is a chart showing timing results at various over-voltages with an array of 4×4×20 mm crystals on a low dark count rate 3×3 channel 4 mm monolithic SiPM array with delayed subtraction. FIG. 14C is a chart showing timing results at various over-voltages with an array of 4×4×20 mm crystals on a low dark count rate 3×3 channel 4 mm monolithic SiPM array with delayed subtraction and time walk correction. These experiments with a low dark count rate monolithic array comprising larger 4 mm SiPMs shows even better block mean crystal timing performance. FIG. 14 shows both uncorrected and digitally corrected timing improvement with 3×3 arrays of 4 mm LSO crystals. Results are similar for 4×4 arrays of 3 mm crystals. These experiments further reveal that even at larger over-voltages up to 1.1 V above the specified $V_{op}$, where device dark count rate is substantially increased, the delayed subtraction correction recovers excellent timing via the common-cathode channel.

Figures 15A, 15B:
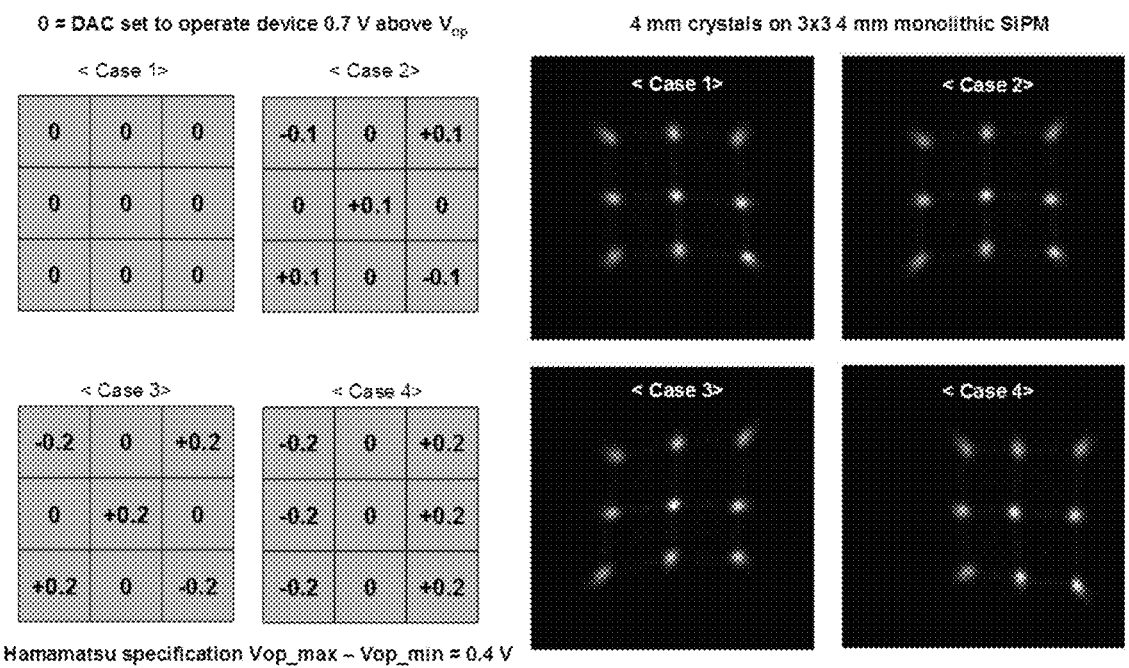
FIG. 15A: is a diagram representing an emulation of device $V_{op}$ variation during single bias voltage operation, according to which a 3×3 array of 4×4×20 mm LSO crystals was used on a 3×3 channel 4 mm monolithic SiPM array.
FIG. 15B: is a diagram of position profiles corresponding to the emulation shown in FIG. 15A of device $V_{op}$ variation during single bias voltage operation, according to which a 3×3 array of 4×4×20 mm LSO crystals was used on a 3×3 channel 4 mm monolithic SiPM array.

FIG. 15A is a diagram representing an emulation of device $V_{op}$ variation during single bias voltage operation, according to which a 3×3 array of 4×4×20 mm LSO crystals was used on a 3×3 channel 4 mm monolithic SiPM array.

Figure 16A:
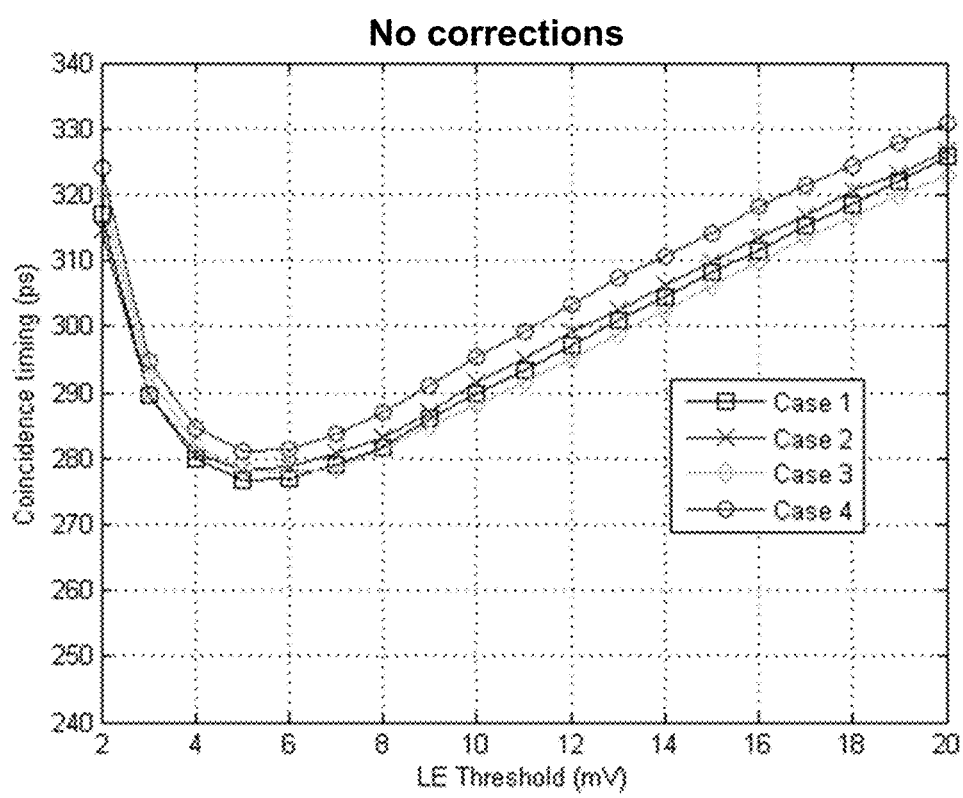
FIG. 16A: is a chart showing the mean crystal timing with no corrections for the $V_{op}$ variation emulation cases shown in FIG. 15A and FIG. 15B.
Figure 16B:
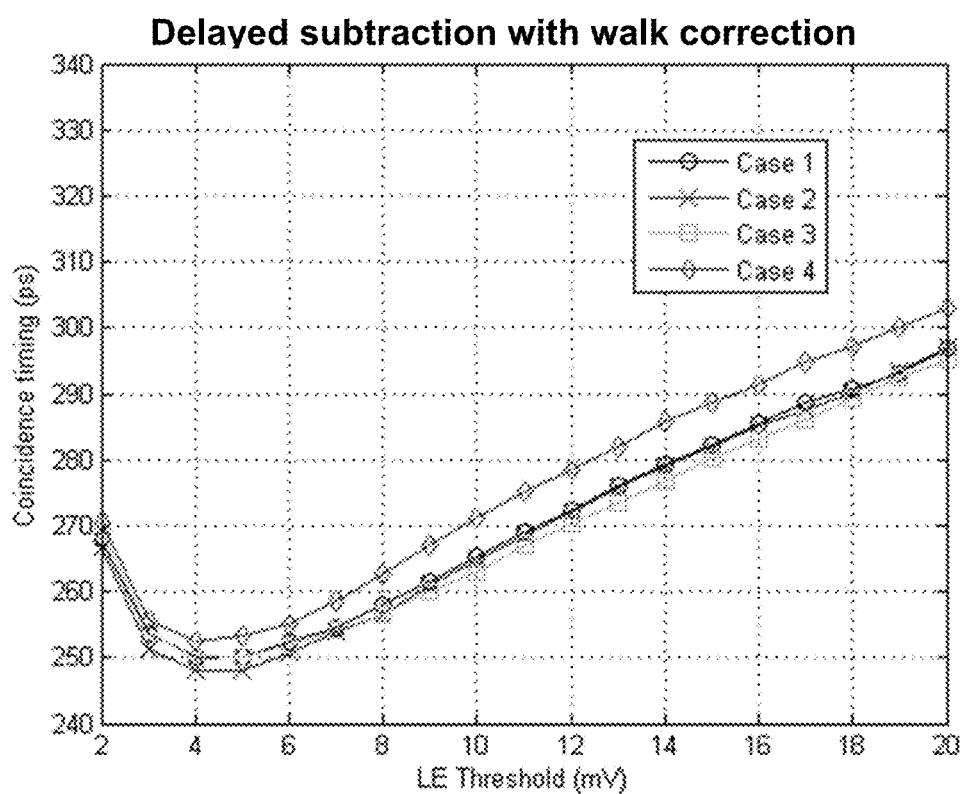
FIG. 16B: is a chart showing the mean crystal timing with delayed subtraction with walk correction for the $V_{op}$ variation emulation cases shown in FIG. 15A and FIG. 15B.

FIG. 15B is a diagram of position profiles corresponding to the emulation shown in FIG. 15A of device $V_{op}$ variation during single bias voltage operation, according to which a 3×3 array of 4×4×20 mm LSO crystals was used on a 3×3 channel 4 mm monolithic SiPM array. In order to evaluate the effect of variations of device operating voltages within an array while operating the entire array at a single bias voltage, exemplary conditions were emulated using the low voltage DAC controls themselves. FIG. 15A and FIG. 15B show the $V_{op}$ deviations emulated and the resulting position profiles. The scintillator pixels are always clearly separable, though significant distortions of the position profiles are apparent. The average energy resolution was degraded by about 0.5 percentage points in the worst case. FIG. 16A is a chart showing the mean crystal timing with no corrections for the $V_{op}$ variation emulation cases shown in FIG. 15A and FIG. 15B. FIG. 16B is a chart showing the mean crystal timing with delayed subtraction with walk correction for the $V_{op}$ variation emulation cases shown in FIG. 15A and FIG. 15B. FIG. 16 shows that the effects on both uncorrected and corrected timing are relatively small, even in the worst case (#4) which emulates a systematic variation across the array which might result from variation across the fabrication wafer. Here we see less than 10 ps of minimum timing variation at a common leading edge threshold for a 0.4 V span of operating voltage, which is Hamamatsu's maximum specification for variation within a 12 mm square monolithic array. This suggests that it might be possible to eliminate individual device bias voltage control, reducing system complexity further, with a small, acceptable loss in timing resolution.

Experimental results combined with both optical/SiPM model Monte Carlo simulations and SPICE circuit simulations suggest that good coincidence resolving time less than or approximately equal to 250 ps is achievable via the common-cathode approach for SiPM arrays of currently available performance, and of larger arrays possibly over 20 mm square of equivalent performance and $V_{op}$ matching. Overall performance based on photopeak event sensitivity and timing is optimized for blocks 16 to 20 mm square. When multiple optimized miniblocks are used together in a PET scanner there will remain some fraction of 511 keV gammas that scatter out of one and into another, resulting in a potential loss in full photopeak energy event sensitivity. Firmware and/or software processing of event position, energy and timing data streams from the miniblocks could be further analyzed to identify such scatter cases. This could be done through time coincidence and photopeak energy qualification of adjacent miniblock energy sums. Corrected position as well as optimal timing for the events could be achieved by various means. For example, multiple time marks with estimated uncertainty as a function of energy deposited can be combined by appropriate weighted averaging to generate time marks with the lowest statistical uncertainty (see Knoll).

Reduction in signal channel density within a scanner can be accomplished by combining common-cathode timing readout miniblocks into optically separated four quadrant groupings. Events which scatter between constituent miniblocks can be validated for photopeak energy using the sum of the miniblock energies, thus recovering otherwise lost sensitivity, while timing for the composite block can be generated using the common-cathode signals of the constituent miniblocks by various means, and a set of position and energy signals can be generated for the entire four-quadrant block by any of a number of different calculations.

Figure 17A:
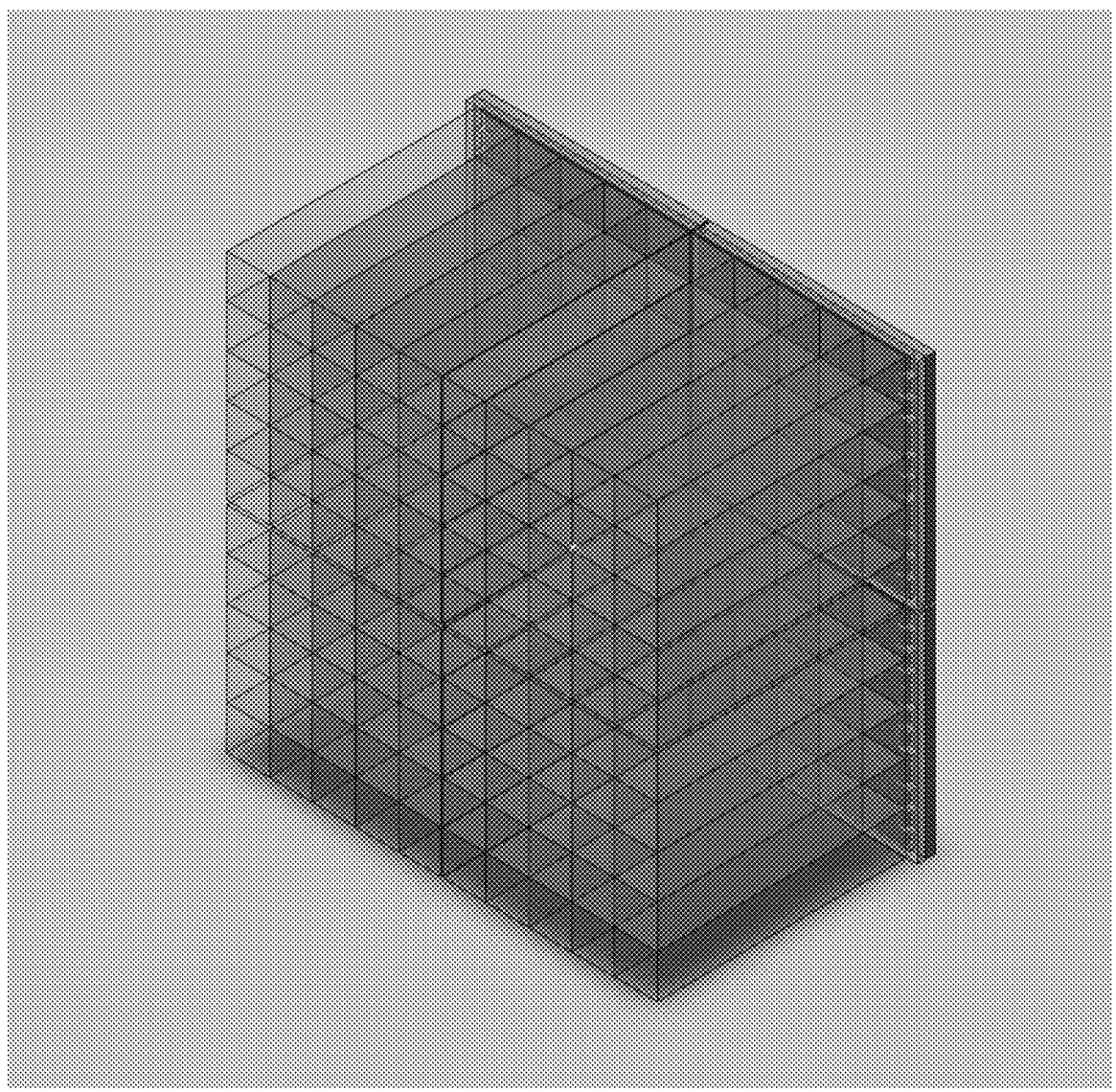
FIG. 17A: is a schematic diagram illustrating a four quadrant detector assembly of miniblocks.
Figure 17B:
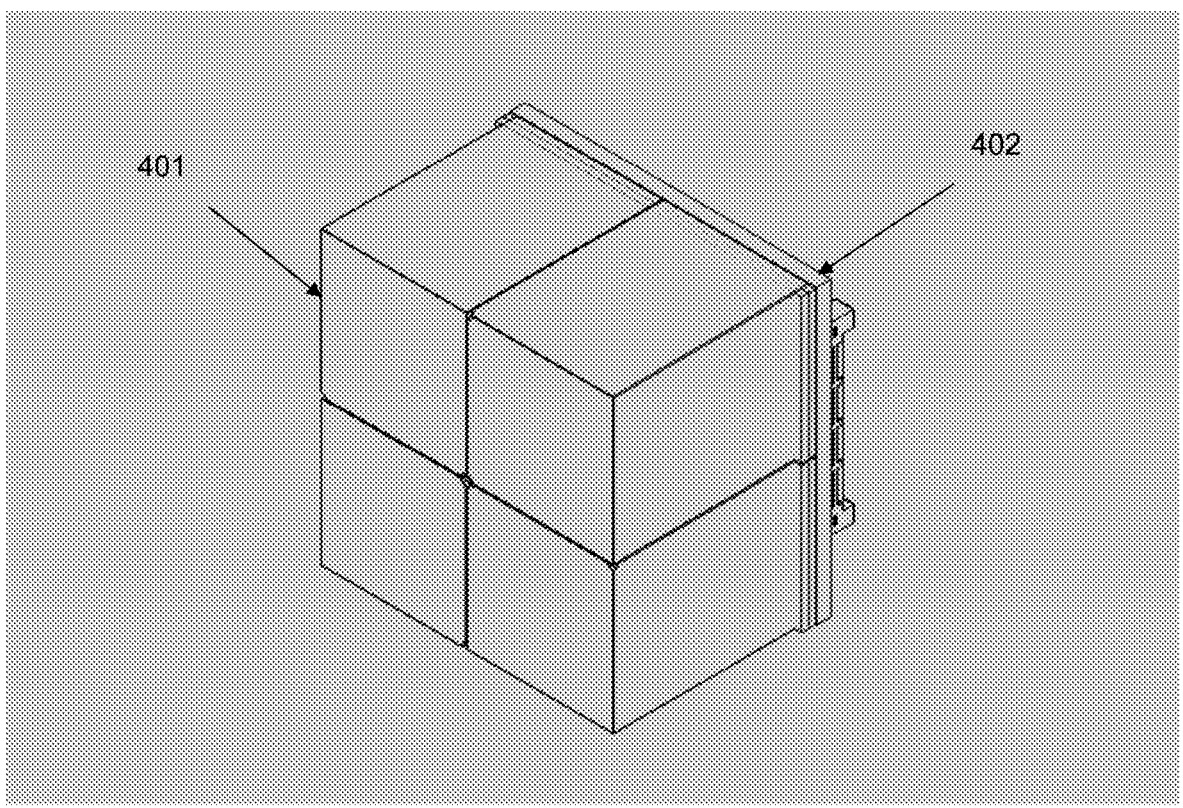
FIG. 17B: is a schematic diagram illustrating a four quadrant detector assembly of miniblocks wrapped with an optically isolating reflector material.

FIG. 17A is a schematic diagram illustrating such a four quadrant detector assembly of miniblocks. FIG. 17A shows four of the miniblocks of FIG. 1. There are practical advantages of such a four-quadrant assembly to make single detector units larger than an optimized sub-block or miniblock. These include the fact that such a detector block represents a potentially more practical testable unit, the possibility of fitting the large block into an existing PET scanner architecture, and also that it could require fewer output signals enabling data stream reduction and/or lower power usage advantageous for demanding applications like MR-PET. FIG. 17B is a schematic diagram illustrating the demarcation between the optically isolating reflector material 401 wrapping each miniblock of FIG. 17A. Each miniblock, comprising a silicon photomultiplier array optically coupled to a scintillator pixel array, is wrapped in optically isolating reflector material 401. The silicon photomultiplier array is connected to an electronic circuit board 402 with a readout circuitry and a system interconnect.

511 keV gammas scattered between the miniblocks can recovered by validating the full photopeak energy of the event using the sum of miniblock energies. One method of timing recovery is to use multiple quadrant time marks with estimated uncertainty as a function of energy deposited and combine them by appropriate weighted averaging to generate a time mark with the lowest statistical uncertainty. A second method of timing recovery is to generate the time mark selecting the signal from the maximum energy miniblock using an appropriate decoding circuit, since it has the least timing uncertainty due to having the largest number of photons contributing. A third possible method of timing recovery is to use the time mark from the first quadrant to generate one, since that will most likely come from the quadrant with the maximum energy deposit, via for example a logical OR of individual miniblock discriminator outputs. Walk correction via individual miniblock energy information, e.g. by lookup table, may also be employed with any of these methods.

Combinations of different numbers of miniblocks, for example 1×2, 2×3, 3×3, etc, into composite detectors or panels are also possible. In any of these cases various methods of combining cathode timing and anode position and energy signals into reduced numbers of signals can be implemented.

Figure 18:
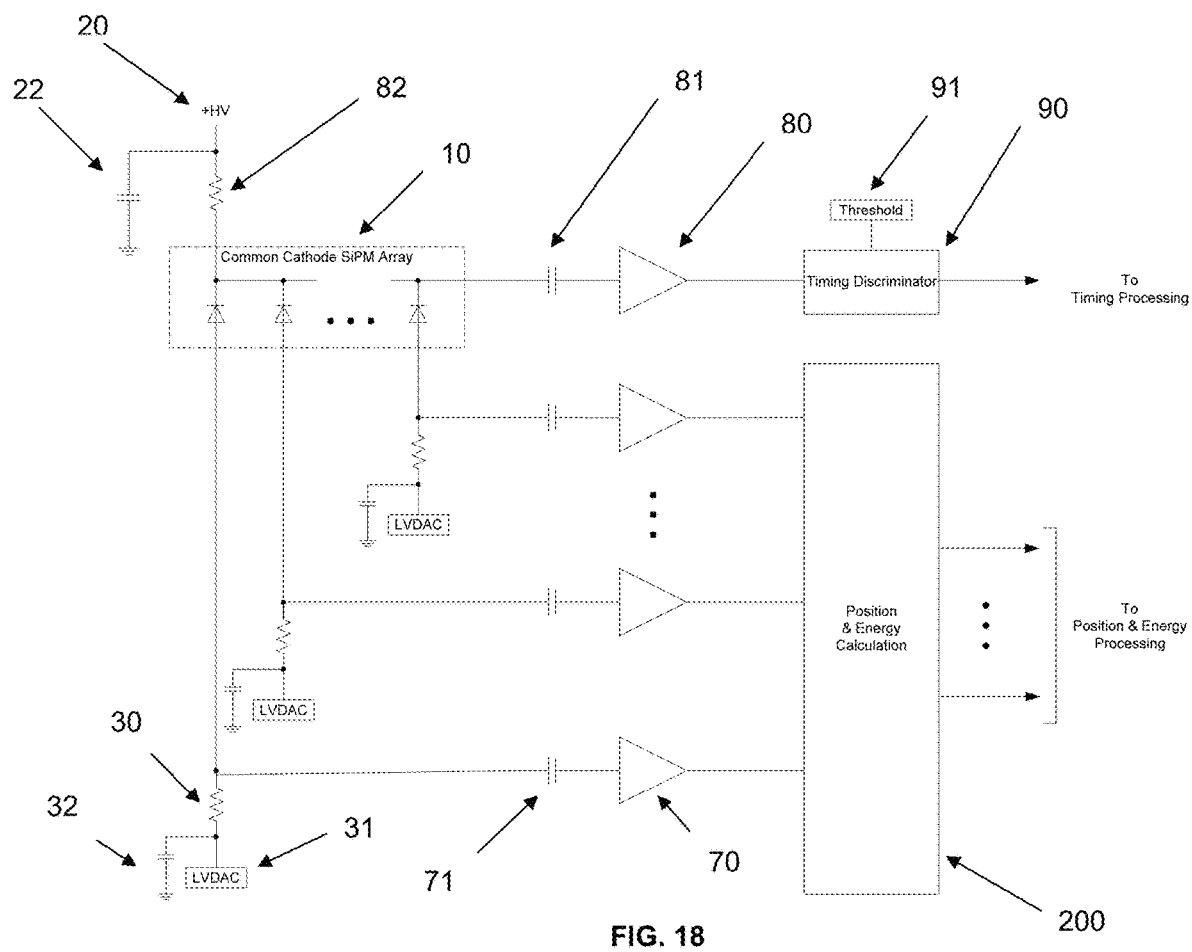
FIG. 18: is a schematic of a basic common-cathode timing/anode position and energy readout with individual SiPM bias control.

FIG. 18 is a schematic of a basic common-cathode timing/anode position and energy readout readout with individual SiPM bias control. Readout schemes such as the basic common-cathode timing and anode position and energy readout of FIG. 18 have been shown to work for existing SiPM device array sizes. A silicon photomultiplier sensor array 10 with common cathode connection can be coupled to a high voltage bias supply 20, having a power supply bypass capacitor 22. An anode load resistor 30 can be provided for each sensor in the silicon photomultiplier sensor array 10. A low voltage digital to analog converter (LVDAC) output 31 can be provided for individual anode gain control. A bypass capacitor 32 can be provided for each low voltage digital to analog converter. An anode energy preamplifier/amplifier 72 can be provided for each sensor in the silicon photomultiplier sensor array 10. An anode preamplifier coupling capacitor 71 can be provided for each sensor in the silicon photomultiplier sensor array 10. A cathode timing preamplifier/amplifier 80, which may comprise one or more stages of amplification and filtering in order to optimize timing performance, can be provided. A cathode preamplifier coupling capacitor 81, which blocks the high voltage cathode bias potential, and cathode bias resistor 82 can be provided for generating cathode timing signal pickoff. A timing discriminator circuit 90 can be provided, having a timing discriminator threshold adjustment 91. Position and energy calculation circuits 200 can be provided to convert all of the anode signals for position and energy processing. These circuits may combine the anode signal information in any of a number of ways to multiplexing them into fewer signals to be digitized, and also may be limit them to appropriate bandwidths for input to free running or triggered sampling digitizers for subsequent digital calculation.

Figure 19:
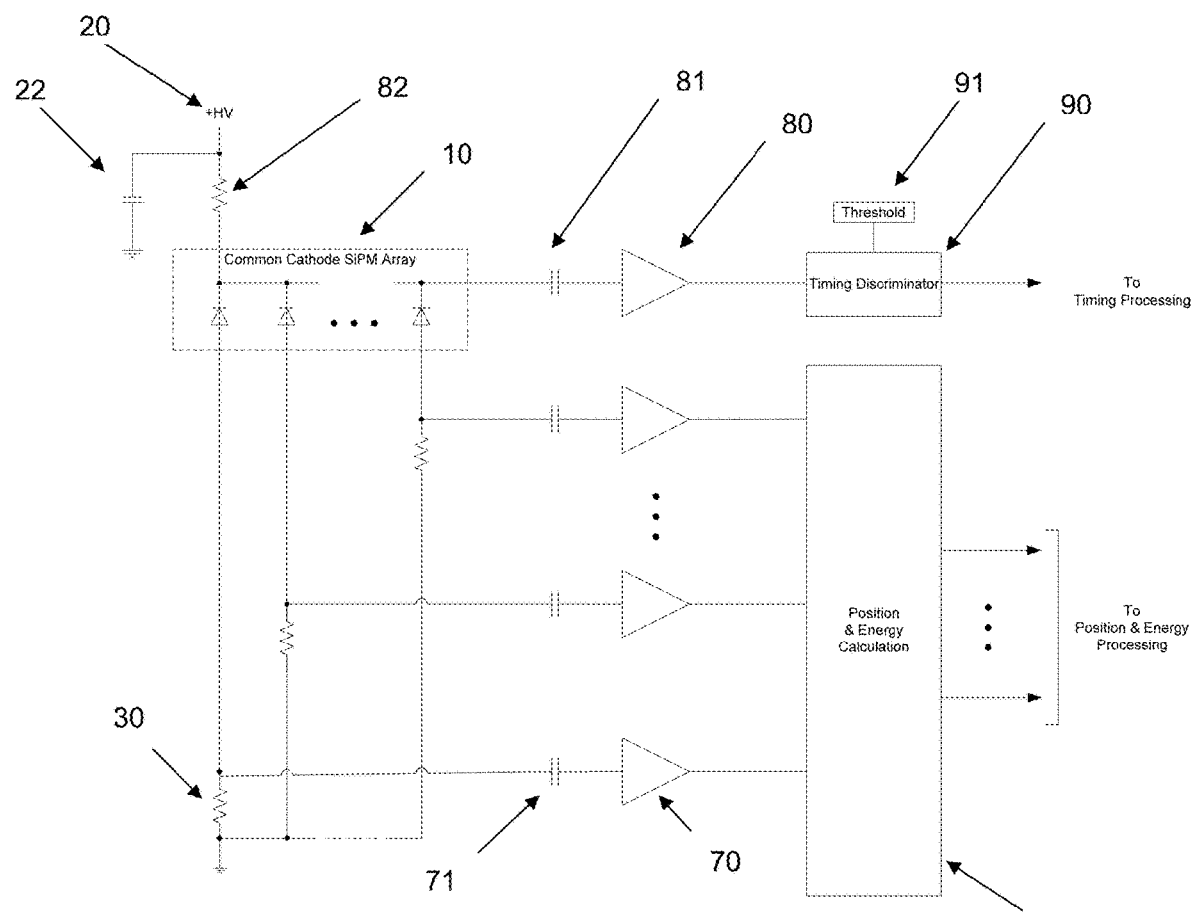
FIG. 19: is a schematic of a common-cathode timing/anode position and energy readout with common SiPM bias control.

FIG. 19 is a schematic of a common-cathode timing/anode position and energy readout with common SiPM bias control. The configuration of FIG. 19 is suggested by results showing that it is feasible to operate arrays of sufficiently closely matched SiPMs at a single bias voltage while still maintaining good timing performance. A silicon photomultiplier sensor array 10 with common cathode connection can be coupled to a high voltage bias supply 20, having a power supply bypass capacitor 22. An anode load resistor 30 can be provided for each sensor in the silicon photomultiplier sensor array 10. Each anode load resistor 30 can be coupled to ground potential as shown so that every sensor in the silicon photomultiplier array 10 is biased by the same total high voltage potential, thus simplifying the necessary circuitry. An anode energy preamplifier/amplifier 72 can be provided for each sensor in the silicon photomultiplier sensor array 10. An anode preamplifier coupling capacitor 71 can be provided for each sensor in the silicon photomultiplier sensor array 10. A cathode timing preamplifier/amplifier 80, which may comprise one or more stages of amplification and filtering in order to optimize timing performance, can be provided. A cathode preamplifier coupling capacitor 81, which blocks the high voltage cathode bias potential, and cathode bias resistor 82 can be provided for generating cathode timing signal pickoff. A timing discriminator circuit 90 can be provided, having a timing discriminator threshold adjustment 91. Position and energy calculation circuits 200 can be provided to convert all of the anode signals for position and energy processing. These circuits may combine the anode signal information in any of a number of ways to multiplexing them into fewer signals to be digitized, and also may be limit them to appropriate bandwidths for input to free running or triggered sampling digitizers for subsequent digital calculation.

Figure 20:
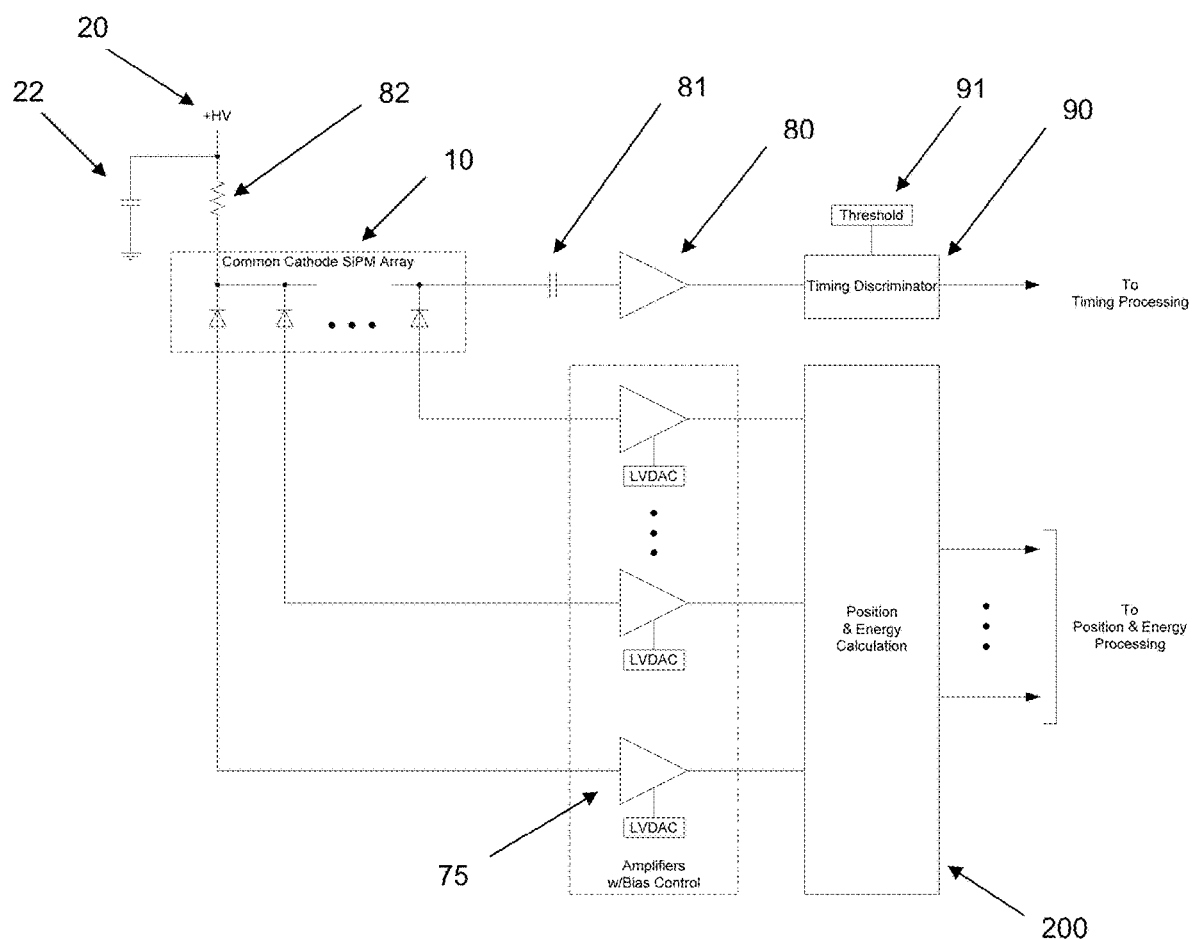
FIG. 20: is a schematic of a common-cathode timing/anode position and energy readout employing direct-coupled anode amplifiers with bias control.

FIG. 20 is a schematic of a common-cathode timing/anode position and energy readout employing direct-coupled anode amplifiers with bias control. This configuration is desirable because it eliminates the need for many components, specifically the anode load resistors 30 and anode preamplifier coupling capacitors 71 of FIG. 18. A silicon photomultiplier sensor array 10 with common cathode connection can be coupled to a high voltage bias supply 20, having a power supply bypass capacitor 22. A direct-coupled anode energy preamplifier/amplifier with low voltage digital to analog converter input bias voltage control 75 can be provided for each sensor in the silicon photomultiplier sensor array 10. A cathode timing preamplifier/amplifier 80, which may comprise one or more stages of amplification and filtering in order to optimize timing performance, can be provided. A cathode preamplifier coupling capacitor 81, which blocks the high voltage cathode bias potential, and cathode bias resistor 82 can be provided for generating cathode timing signal pickoff. A timing discriminator circuit 90 can be provided, having a timing discriminator threshold adjustment 91. Position and energy calculation circuits 200 can be provided to convert all of the anode signals for position and energy processing. These circuits may combine the anode signal information in any of a number of ways to multiplexing them into fewer signals to be digitized, and also may be limit them to appropriate bandwidths for input to free running or triggered sampling digitizers for subsequent digital calculation.

Although the present invention has been described in considerable detail with reference to certain preferred versions thereof, other versions are possible. Therefore, the spirit and scope of the appended claims should not be limited to the description of the preferred versions contained herein.

The reader's attention is directed to all papers and documents which are filed concurrently with this specification and which are open to public inspection with this specification, and the contents of all such papers and documents are incorporated herein by reference.

All the features disclosed in this specification (including any accompanying claims, abstract, and drawings) may be replaced by alternative features serving the same, equivalent or similar purpose, unless expressly stated otherwise. Thus, unless expressly stated otherwise, each feature disclosed is one example only of a generic series of equivalent or similar features.

Any element in a claim that does not explicitly state "means for" performing a specified function, or "step for" performing a specific function, is not to be interpreted as a "means" or "step" clause as specified in 35 U.S.C § 112, sixth paragraph. In particular, the use of "step of" in the claims herein is not intended to invoke the provisions of 35 U.S.C § 112, sixth paragraph.

What is claimed is:

1. A scintillation detector, comprising:
an array of silicon photomultipliers (SiPMs) mounted on a substrate;
an array of individual scintillator crystals optically coupled to said array of SiPMs;
a plurality of said individual scintillator crystals of said array being optically coupled to each other by an air gap; and
said array of scintillator crystals being wrapped by an external reflector; where each scintillation detector comprises sub-block quadrants; where each sub-block quadrant is optically separated from a neighboring sub-block quadrant by an optically isolating reflector material;
wherein each of a SiPM cathode output is coupled to a common cathode output lead, and an anode output is coupled to individual anode output leads; and SiPM signal processing circuitry, including:
scintillation event timing computation circuitry configured to receive a common cathode output signal from said common cathode output lead, and configured to compute timing of a scintillation event incident on said scintillator crystal array from said common cathode output signal, and
scintillation event position and energy computation circuitry configured to receive individual anode output signals from said individual anode output leads, and configured to compute position and energy of said scintillation event incident on said scintillator crystal array from said individual anode output signals: where scintillation events are validated for total energy by summing energy contributions from the sub-quadrants; and wherein a trigger is generated from a timing signal of each sub-block quadrant with a highest energy deposition.

2. The scintillation detector of claim 1, wherein said scintillator crystals are composed of LSO.

3. The scintillator detector of claim 1, wherein said scintillator crystal array is coupled to said SiPM array via an optical coupling element.

4. A PET scanner, comprising a plurality of scintillation detectors as set forth in claim 1.

5. A PET scanner, comprising a plurality of composite scintillation block detectors as set forth in claim 1.

6. The scintillator detector of claim 1, wherein at least one of said scintillator crystals of said array is optically isolated from, or has reduced optical coupling to, other scintillator crystals of said array, by interposed optical reflector material.

7. A PET/CT scanner, comprising a plurality of scintillation detectors as set forth in claim 1.

8. A PET/MR scanner, comprising a plurality of scintillation detectors as set forth in claim 1.

9. A PET scanner, comprising a plurality of composite scintillation block detectors as set forth in claim 2.

10. A PET/CT scanner, comprising a plurality of composite scintillation block detectors as set forth in claim 1.

11. A PET/MR scanner, comprising a plurality of composite scintillation block detectors as set forth in claim 1.

12. A pixelated scintillation block detector, comprising:
an array of silicon photomultiplier (SiPM) light sensors with common-cathode signal timing pickoff and individual anode signal position and energy determination; where each array of silicon photomultiplier light sensors comprises sub-block quadrants where each sub-block quadrant is optically separated from a neighboring quadrant by an optically isolating reflector material and
an array of optically air-coupled scintillation pixels, the array being wrapped in reflector material and the array being optically coupled to said array of SiPM light sensors;
where events are validated for total energy by summing energy contributions from the sub-quadrants;
wherein a trigger is generated from a timing signal of each sub-quadrant with highest energy deposition or a first timing signal is derived from a sub-quadrant time-pickoff signal.

13. The pixelated scintillation block detector of claim 12, wherein said scintillator pixels are composed of LSO.

14. The pixelated scintillation block detector of claim 12, wherein said array of optically air-coupled scintillation pixels is coupled to said SiPM array via an optical coupling element.

15. A composite scintillation block detector, comprising sub-block quadrants each comprising a pixelated scintillation block detector as claimed in claim 12.

16. A PET scanner, comprising a plurality of pixelated scintillation block detector as set forth in claim 12.

17. The pixelated scintillation block detector of claim 12, wherein at least one of said scintillator pixels of said array is optically isolated from, or has reduced optical coupling to, other scintillator crystals of said array, by interposed optical reflector material.

18. A PET/CT scanner, comprising a plurality of pixelated scintillation block detectors as set forth in claim 12.

19. A PET/MR scanner, comprising a plurality of pixelated scintillation block detectors as set forth in claim 12.

* * * * *